(12) United States Patent
Kaiser et al.

(10) Patent No.: US 8,562,647 B2
(45) Date of Patent: Oct. 22, 2013

(54) METHOD AND APPARATUS FOR SECURING SOFT TISSUE TO BONE

(75) Inventors: Ryan A. Kaiser, Leesburg, IN (US);
Gregory J. Denham, Warsaw, IN (US);
Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 12/915,962

(22) Filed: Oct. 29, 2010

(65) Prior Publication Data

US 2011/0098727 A1  Apr. 28, 2011

Related U.S. Application Data

(63) Continuation-in-part of application No. 12/719,337, filed on Mar. 8, 2010, which is a continuation-in-part of application No. 12/489,168, filed on Jun. 22, 2009, which is a continuation-in-part of application No. 12/474,802, filed on May 29, 2009, now Pat. No. 8,088,130, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, (Continued)

(51) Int. Cl.
*A61B 17/04* (2006.01)
*A61B 17/84* (2006.01)
*A61F 2/08* (2006.01)

(52) U.S. Cl.
USPC .......................................... 606/232; 606/300

(58) Field of Classification Search
USPC ........... 606/139, 151, 232, 60, 300, 301, 313;
128/898; 623/13.11, 13.14, 623/13.17–13.2, 19.11
See application file for complete search history.

(56) References Cited

U.S. PATENT DOCUMENTS

| 65,499 A | 6/1867 | Miller |
|---|---|---|
| 126,366 A | 4/1872 | Wills |

(Continued)

FOREIGN PATENT DOCUMENTS

| AU | 4957264 | 3/1966 |
|---|---|---|
| AU | 440266 | 10/1967 |

(Continued)

OTHER PUBLICATIONS

"Arthroscopic Meniscal Repair using the Meniscal Cinch™", Surgical Technique brochure. (2008) Arthrex® 6 sheets.

(Continued)

*Primary Examiner* — Dianne Dornbusch
(74) *Attorney, Agent, or Firm* — Harness, Dickey

(57) ABSTRACT

A method and apparatus for securing soft tissue to bone can include forming a bore in the bone and carrying a flexible suture anchor into the bore. The flexible anchor can include a passage and can be coupled to a suture construct. The suture construct can include at least one self-locking adjustable loop, and the flexible anchor can include a first profile while being carried into the bore. A shape of the flexible anchor can be changed from the first profile to a second profile forming an anchoring mass to retain the flexible anchor in the bore. Tension can be applied to a portion of the suture construct to reduce a size of the self-locking adjustable loop and secure the soft tissue relative to the flexible anchor and the bone.

35 Claims, 12 Drawing Sheets

Related U.S. Application Data now Pat. No. 8,118,836, and a continuation-in-part of application No. 11/541,506, filed on Sep. 29, 2006, now Pat. No. 7,601,165, application No. 12/915,962, which is a continuation-in-part of application No. 12/570,854, filed on Sep. 30, 2009, which is a continuation-in-part of application No. 12/014,399, filed on Jan. 15, 2008, now Pat. No. 7,909,851, application No. 12/915,962, which is a continuation-in-part of application No. 12/702,067, filed on Feb. 8, 2010, which is a continuation of application No. 11/541,505, filed on Sep. 29, 2006, now Pat. No. 7,658,751, application No. 12/915,962, which is a continuation-in-part of application No. 12/196,398, filed on Aug. 22, 2008, now Pat. No. 7,959,650, which is a continuation-in-part of application No. 11/784,821, filed on Apr. 10, 2007.

(56) References Cited

U.S. PATENT DOCUMENTS

| | | |
|---|---|---|
| 233,475 A | 10/1880 | Cook et al. |
| 261,501 A | 7/1882 | Vandermark |
| 268,407 A | 12/1882 | Hughes |
| 330,087 A | 11/1885 | Binns |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 401,677 A | 11/1933 | Roeder |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |

(56) References Cited

U.S. PATENT DOCUMENTS

| | | |
|---|---|---|
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |

(56) References Cited

U.S. PATENT DOCUMENTS

| | | |
|---|---|---|
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,192,282 A | 3/1993 | Draenert et al. |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |

(56) References Cited

U.S. PATENT DOCUMENTS

| | | |
|---|---|---|
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,397,356 A | 3/1995 | Goble et al. |
| 5,403,328 A | 4/1995 | Shallman |
| 5,403,329 A | 4/1995 | Hinchcliffe |
| 5,403,348 A * | 4/1995 | Bonutti .................. 606/232 |
| 5,405,359 A | 4/1995 | Pierce |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |

(56) References Cited

U.S. PATENT DOCUMENTS

| | | | |
|---|---|---|---|
| 5,643,321 | A | 7/1997 | McDevitt |
| 5,645,546 | A | 7/1997 | Fard |
| 5,645,547 | A | 7/1997 | Coleman |
| 5,645,568 | A | 7/1997 | Chervitz et al. |
| 5,645,588 | A | 7/1997 | Graf et al. |
| 5,647,874 | A * | 7/1997 | Hayhurst ............... 606/232 |
| 5,649,959 | A | 7/1997 | Hannam et al. |
| 5,649,963 | A | 7/1997 | McDevitt |
| 5,658,289 | A | 8/1997 | Boucher et al. |
| 5,658,299 | A | 8/1997 | Hart |
| 5,658,313 | A | 8/1997 | Thal |
| 5,662,658 | A | 9/1997 | Wenstrom, Jr. |
| 5,662,663 | A | 9/1997 | Shallman |
| 5,662,681 | A | 9/1997 | Nash et al. |
| 5,665,112 | A | 9/1997 | Thal |
| 5,667,513 | A | 9/1997 | Torrie et al. |
| 5,671,695 | A | 9/1997 | Schroeder |
| 5,674,224 | A | 10/1997 | Howell et al. |
| 5,679,723 | A | 10/1997 | Cooper et al. |
| 5,681,334 | A | 10/1997 | Evans et al. |
| 5,681,352 | A | 10/1997 | Clancy, III et al. |
| 5,683,419 | A | 11/1997 | Thal |
| 5,688,284 | A | 11/1997 | Chervitz et al. |
| 5,688,285 | A | 11/1997 | Yamada et al. |
| 5,690,655 | A | 11/1997 | Hart et al. |
| 5,690,676 | A | 11/1997 | DiPoto et al. |
| 5,690,678 | A | 11/1997 | Johnson |
| 5,693,046 | A | 12/1997 | Songer et al. |
| 5,695,497 | A | 12/1997 | Stahelin et al. |
| 5,697,929 | A | 12/1997 | Mellinger |
| 5,699,657 | A * | 12/1997 | Paulson ............... 57/22 |
| 5,702,397 | A | 12/1997 | Goble et al. |
| 5,702,422 | A | 12/1997 | Stone |
| 5,702,462 | A | 12/1997 | Oberlander |
| 5,707,373 | A | 1/1998 | Sevrain et al. |
| 5,711,969 | A | 1/1998 | Patel et al. |
| 5,713,005 | A | 1/1998 | Proebsting |
| 5,713,897 | A | 2/1998 | Goble et al. |
| 5,713,904 | A | 2/1998 | Errico et al. |
| 5,713,905 | A | 2/1998 | Goble et al. |
| 5,713,921 | A | 2/1998 | Bonutti |
| 5,716,359 | A | 2/1998 | Ojima et al. |
| 5,716,397 | A | 2/1998 | Myers |
| 5,718,717 | A | 2/1998 | Bonutti |
| 5,720,747 | A | 2/1998 | Burke |
| 5,720,765 | A | 2/1998 | Thal |
| 5,720,766 | A | 2/1998 | Zang et al. |
| 5,722,976 | A | 3/1998 | Brown |
| 5,725,529 | A | 3/1998 | Nicholson et al. |
| 5,725,549 | A | 3/1998 | Lam |
| 5,725,556 | A | 3/1998 | Moser et al. |
| 5,725,581 | A | 3/1998 | Brånemark et al. |
| 5,725,582 | A | 3/1998 | Bevan et al. |
| 5,726,722 | A | 3/1998 | Uehara et al. |
| 5,728,107 | A | 3/1998 | Zlock et al. |
| 5,728,109 | A | 3/1998 | Schulze et al. |
| 5,728,136 | A | 3/1998 | Thal |
| 5,733,293 | A | 3/1998 | Scirica et al. |
| 5,733,306 | A | 3/1998 | Bonutti |
| 5,733,307 | A | 3/1998 | Dinsdale |
| 5,735,875 | A | 4/1998 | Bonutti et al. |
| 5,741,259 | A | 4/1998 | Chan |
| 5,741,260 | A | 4/1998 | Songer et al. |
| 5,741,281 | A | 4/1998 | Martin et al. |
| 5,743,912 | A | 4/1998 | Lahille et al. |
| 5,746,751 | A | 5/1998 | Sherts |
| 5,746,752 | A | 5/1998 | Burkhart |
| 5,746,754 | A | 5/1998 | Chan |
| 5,749,898 | A | 5/1998 | Schulze et al. |
| 5,755,729 | A | 5/1998 | de la Torre et al. |
| 5,755,791 | A | 5/1998 | Whitson et al. |
| 5,766,176 | A | 6/1998 | Duncan |
| 5,766,218 | A | 6/1998 | Arnott |
| 5,766,250 | A | 6/1998 | Chervitz et al. |
| 5,769,894 | A | 6/1998 | Ferragamo |
| 5,769,899 | A | 6/1998 | Schwartz et al. |
| 5,772,673 | A | 6/1998 | Cuny et al. |
| 5,776,196 | A | 7/1998 | Matsuzaki et al. |
| 5,782,845 | A | 7/1998 | Shewchuk |
| 5,782,862 | A | 7/1998 | Bonutti |
| 5,782,864 | A | 7/1998 | Lizardi |
| 5,782,866 | A | 7/1998 | Wenstrom, Jr. |
| 5,785,714 | A | 7/1998 | Morgan et al. |
| 5,792,142 | A | 8/1998 | Galitzer |
| 5,792,149 | A | 8/1998 | Sherts et al. |
| 5,796,127 | A | 8/1998 | Hayafuji et al. |
| 5,797,915 | A | 8/1998 | Pierson, III et al. |
| 5,797,916 | A | 8/1998 | McDowell |
| 5,797,928 | A | 8/1998 | Kogasaka |
| 5,800,407 | A | 9/1998 | Eldor et al. |
| 5,810,824 | A | 9/1998 | Chan |
| 5,810,848 | A | 9/1998 | Hayhurst |
| 5,814,056 | A | 9/1998 | Prosst et al. |
| 5,814,069 | A | 9/1998 | Schulze et al. |
| 5,814,070 | A | 9/1998 | Borzone et al. |
| 5,814,072 | A | 9/1998 | Bonutti |
| 5,814,073 | A | 9/1998 | Bonutti |
| 5,823,980 | A | 10/1998 | Kopfer |
| 5,824,011 | A | 10/1998 | Stone et al. |
| 5,824,066 | A | 10/1998 | Gross |
| 5,830,234 | A | 11/1998 | Wojciechowicz et al. |
| 5,843,084 | A | 12/1998 | Hart et al. |
| 5,845,645 | A | 12/1998 | Bonutti |
| 5,846,254 | A | 12/1998 | Schulze et al. |
| 5,848,983 | A | 12/1998 | Basaj et al. |
| 5,849,012 | A | 12/1998 | Abboudi |
| 5,860,973 | A | 1/1999 | Michelson |
| 5,860,978 | A | 1/1999 | McDevitt et al. |
| 5,868,740 | A | 2/1999 | LeVeen et al. |
| 5,868,748 | A | 2/1999 | Burke |
| 5,868,789 | A | 2/1999 | Huebner |
| 5,871,484 | A | 2/1999 | Spievack et al. |
| 5,871,486 | A | 2/1999 | Huebner et al. |
| 5,871,490 | A | 2/1999 | Schulze et al. |
| 5,885,294 | A | 3/1999 | Pedlick et al. |
| 5,891,168 | A | 4/1999 | Thal |
| 5,893,592 | A | 4/1999 | Schulze et al. |
| 5,895,395 | A | 4/1999 | Yeung |
| 5,897,564 | A | 4/1999 | Schulze et al. |
| 5,897,574 | A | 4/1999 | Bonutti |
| 5,899,902 | A | 5/1999 | Brown et al. |
| 5,899,938 | A | 5/1999 | Sklar et al. |
| 5,908,421 | A | 6/1999 | Beger et al. |
| 5,908,436 | A | 6/1999 | Cuschieri et al. |
| 5,910,148 | A | 6/1999 | Reimels et al. |
| 5,911,721 | A | 6/1999 | Nicholson et al. |
| 5,918,604 | A | 7/1999 | Whelan |
| 5,921,986 | A | 7/1999 | Bonutti |
| 5,925,008 | A | 7/1999 | Douglas |
| 5,928,231 | A | 7/1999 | Klein et al. |
| 5,928,267 | A | 7/1999 | Bonutti et al. |
| RE36,289 | E | 8/1999 | Le et al. |
| 5,931,838 | A | 8/1999 | Vito |
| 5,931,844 | A | 8/1999 | Thompson et al. |
| 5,931,869 | A | 8/1999 | Boucher et al. |
| 5,935,119 | A | 8/1999 | Guy et al. |
| 5,935,133 | A | 8/1999 | Wagner et al. |
| 5,935,149 | A | 8/1999 | Ek |
| 5,938,668 | A | 8/1999 | Scirica et al. |
| 5,941,439 | A | 8/1999 | Kammerer et al. |
| 5,941,900 | A | 8/1999 | Bonutti |
| 5,944,739 | A | 8/1999 | Zlock et al. |
| 5,946,783 | A | 9/1999 | Plociennik et al. |
| 5,947,915 | A | 9/1999 | Thibodo, Jr. |
| 5,947,982 | A | 9/1999 | Duran |
| 5,947,999 | A | 9/1999 | Groiso |
| 5,948,002 | A | 9/1999 | Bonutti |
| 5,951,559 | A | 9/1999 | Burkhart |
| 5,951,560 | A | 9/1999 | Simon et al. |
| 5,954,747 | A | 9/1999 | Clark |
| 5,957,953 | A | 9/1999 | DiPoto et al. |
| 5,961,520 | A | 10/1999 | Beck, Jr. et al. |
| 5,961,521 | A | 10/1999 | Roger et al. |
| 5,961,524 | A | 10/1999 | Crombie |

(56) References Cited

U.S. PATENT DOCUMENTS

| | | |
|---|---|---|
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A * | 11/1999 | Fumex ............ 606/232 |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A * | 3/2000 | Meislin ............ 606/213 |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 * | 8/2001 | Cassidy et al. ............ 623/16.11 |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 * | 10/2001 | Foerster ............ 606/224 |
| 6,299,615 B1 | 10/2001 | Huebner |
| 6,302,888 B1 | 10/2001 | Mellinger et al. |
| 6,302,899 B1 | 10/2001 | Johnson et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |

(56) References Cited

U.S. PATENT DOCUMENTS

| | | |
|---|---|---|
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 * | 11/2002 | Johnson et al. ............... 606/216 |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 * | 1/2003 | Fumex ........................ 606/232 |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 * | 12/2003 | Foerster et al. ............... 606/327 |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 * | 2/2004 | West et al. .................... 606/232 |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 * | 8/2004 | Foerster ........................ 606/326 |
| 6,770,084 B1 | 8/2004 | Bain et al. |
| 6,773,450 B2 | 8/2004 | Leung et al. |

(56) References Cited

U.S. PATENT DOCUMENTS

| | | |
|---|---|---|
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,201,722 B2 | 4/2007 | Krueger |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 * | 2/2008 | Burkhart et al. ............... 606/232 |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,494,506 B2 | 2/2009 | Brulez et al. |
| D587,807 S | 3/2009 | Wolf et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,597,705 B2 | 10/2009 | Forsberg et al. |
| 7,601,165 B2 | 10/2009 | Stone |
| 7,604,636 B1 * | 10/2009 | Walters et al. .................. 606/80 |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,731,732 B2 | 6/2010 | Ken |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,803,173 B2 | 9/2010 | Burkhart et al. |
| 7,819,895 B2 | 10/2010 | Ginn et al. |
| 7,828,850 B2 | 11/2010 | Cauthen, III et al. |
| 7,857,830 B2 | 12/2010 | Stone et al. |
| 7,875,058 B2 | 1/2011 | Holmes, Jr. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 * | 7/2011 | Burkhart ....................... 606/232 |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 8,162,997 B2 | 4/2012 | Struhl |
| 8,167,906 B2 * | 5/2012 | Cauldwell et al. ............ 606/232 |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,361,113 B2 | 1/2013 | Stone et al. |
| 8,409,253 B2 | 4/2013 | Stone et al. |
| 2001/0010005 A1 | 7/2001 | Kammerer et al. |
| 2001/0014825 A1 | 8/2001 | Burke et al. |
| 2001/0019649 A1 | 9/2001 | Field et al. |

(56) References Cited

U.S. PATENT DOCUMENTS

| | | |
|---|---|---|
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2003/0229396 A1 | 12/2003 | Andrews |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267361 A1 | 12/2004 | Donnelly et al. |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1* | 2/2005 | Bojarski et al. ............... 606/228 |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |

(56) References Cited

U.S. PATENT DOCUMENTS

| | | | | |
|---|---|---|---|---|
| 2005/0096743 | A1 | 5/2005 | Schmieding et al. | |
| 2005/0101957 | A1 | 5/2005 | Buskirk et al. | |
| 2005/0107795 | A1 | 5/2005 | Morris et al. | |
| 2005/0107828 | A1 | 5/2005 | Reese | |
| 2005/0119531 | A1 | 6/2005 | Sharratt | |
| 2005/0119696 | A1 | 6/2005 | Walters et al. | |
| 2005/0124996 | A1 | 6/2005 | Hearn | |
| 2005/0125031 | A1 | 6/2005 | Pipenhagen et al. | |
| 2005/0125036 | A1 | 6/2005 | Roby | |
| 2005/0125073 | A1 | 6/2005 | Orban et al. | |
| 2005/0131413 | A1 | 6/2005 | O'Driscoll et al. | |
| 2005/0137600 | A1 | 6/2005 | Jacobs et al. | |
| 2005/0137624 | A1* | 6/2005 | Fallman | 606/213 |
| 2005/0149033 | A1 | 7/2005 | McGuire et al. | |
| 2005/0149122 | A1 | 7/2005 | McDevitt et al. | |
| 2005/0149187 | A1 | 7/2005 | Clark et al. | |
| 2005/0159812 | A1 | 7/2005 | Dinger et al. | |
| 2005/0165416 | A1 | 7/2005 | Bojarski et al. | |
| 2005/0165482 | A1 | 7/2005 | Goldhahn et al. | |
| 2005/0171603 | A1 | 8/2005 | Justin et al. | |
| 2005/0187565 | A1 | 8/2005 | Baker et al. | |
| 2005/0187577 | A1 | 8/2005 | Selvitelli et al. | |
| 2005/0187635 | A1 | 8/2005 | Metzger | |
| 2005/0203620 | A1 | 9/2005 | Steiner et al. | |
| 2005/0222618 | A1 | 10/2005 | Dreyfuss et al. | |
| 2005/0222619 | A1 | 10/2005 | Dreyfuss et al. | |
| 2005/0228448 | A1* | 10/2005 | Li | 606/232 |
| 2005/0240198 | A1 | 10/2005 | Albertson et al. | |
| 2005/0251159 | A1 | 11/2005 | Ewers et al. | |
| 2005/0251177 | A1* | 11/2005 | Saadat et al. | 606/153 |
| 2005/0251208 | A1 | 11/2005 | Elmer et al. | |
| 2005/0251210 | A1 | 11/2005 | Westra et al. | |
| 2005/0267479 | A1 | 12/2005 | Morgan et al. | |
| 2005/0267533 | A1 | 12/2005 | Gertner | |
| 2005/0277939 | A1 | 12/2005 | Miller | |
| 2005/0277961 | A1 | 12/2005 | Stone et al. | |
| 2005/0283040 | A1 | 12/2005 | Greenhalgh | |
| 2005/0283156 | A1 | 12/2005 | Schmieding et al. | |
| 2005/0283158 | A1 | 12/2005 | West | |
| 2005/0283192 | A1 | 12/2005 | Torrie et al. | |
| 2006/0004410 | A1 | 1/2006 | Nobis et al. | |
| 2006/0015103 | A1 | 1/2006 | Burke | |
| 2006/0015106 | A1 | 1/2006 | Lerch et al. | |
| 2006/0015107 | A1 | 1/2006 | Sklar | |
| 2006/0030884 | A1 | 2/2006 | Yeung et al. | |
| 2006/0030948 | A1 | 2/2006 | Manrique et al. | |
| 2006/0036265 | A1 | 2/2006 | Dant | |
| 2006/0052787 | A1 | 3/2006 | Re et al. | |
| 2006/0052818 | A1 | 3/2006 | Drake et al. | |
| 2006/0064125 | A1 | 3/2006 | Henderson et al. | |
| 2006/0064126 | A1 | 3/2006 | Fallin et al. | |
| 2006/0069334 | A1 | 3/2006 | Moskowitz | |
| 2006/0079904 | A1* | 4/2006 | Thal | 606/72 |
| 2006/0084943 | A1 | 4/2006 | Rosenman et al. | |
| 2006/0085000 | A1 | 4/2006 | Mohr et al. | |
| 2006/0089672 | A1 | 4/2006 | Martinek | |
| 2006/0095130 | A1 | 5/2006 | Caborn et al. | |
| 2006/0095131 | A1 | 5/2006 | Justin et al. | |
| 2006/0100627 | A1 | 5/2006 | Stone et al. | |
| 2006/0100637 | A1 | 5/2006 | Rathbun et al. | |
| 2006/0106423 | A1 | 5/2006 | Weisel et al. | |
| 2006/0111721 | A1 | 5/2006 | Puricelli et al. | |
| 2006/0116685 | A1 | 6/2006 | Urbanski et al. | |
| 2006/0121084 | A1 | 6/2006 | Borden et al. | |
| 2006/0122611 | A1 | 6/2006 | Morales et al. | |
| 2006/0135958 | A1 | 6/2006 | Marissen et al. | |
| 2006/0149258 | A1 | 7/2006 | Sousa | |
| 2006/0149266 | A1 | 7/2006 | Cordasco | |
| 2006/0155287 | A1 | 7/2006 | Montgomery et al. | |
| 2006/0161161 | A1 | 7/2006 | Shifrin et al. | |
| 2006/0167458 | A1 | 7/2006 | Gabele | |
| 2006/0167481 | A1 | 7/2006 | Baker et al. | |
| 2006/0167482 | A1 | 7/2006 | Swain et al. | |
| 2006/0173492 | A1 | 8/2006 | Akerfeldt et al. | |
| 2006/0178680 | A1 | 8/2006 | Nelson et al. | |
| 2006/0189993 | A1 | 8/2006 | Stone | |
| 2006/0190042 | A1 | 8/2006 | Stone et al. | |
| 2006/0195101 | A1 | 8/2006 | Stevens | |
| 2006/0200235 | A1 | 9/2006 | Bianchi et al. | |
| 2006/0212055 | A1 | 9/2006 | Karabey et al. | |
| 2006/0229671 | A1 | 10/2006 | Steiner et al. | |
| 2006/0235407 | A1 | 10/2006 | Wang et al. | |
| 2006/0235413 | A1 | 10/2006 | Denham et al. | |
| 2006/0241624 | A1 | 10/2006 | Kizuka et al. | |
| 2006/0247642 | A1 | 11/2006 | Stone et al. | |
| 2006/0253130 | A1 | 11/2006 | Wolniewicz | |
| 2006/0259048 | A1 | 11/2006 | Koseki | |
| 2006/0271192 | A1 | 11/2006 | Olsen et al. | |
| 2006/0276793 | A1 | 12/2006 | Berry | |
| 2006/0276809 | A1 | 12/2006 | Oliveira | |
| 2006/0276841 | A1 | 12/2006 | Barbieri et al. | |
| 2006/0280768 | A1 | 12/2006 | Hwang et al. | |
| 2006/0282082 | A1 | 12/2006 | Fanton et al. | |
| 2006/0282083 | A1 | 12/2006 | Fanton et al. | |
| 2006/0282085 | A1 | 12/2006 | Stone et al. | |
| 2006/0293709 | A1 | 12/2006 | Bojarski et al. | |
| 2007/0005080 | A1 | 1/2007 | Wolniewicz et al. | |
| 2007/0010857 | A1 | 1/2007 | Sugimoto et al. | |
| 2007/0016305 | A1 | 1/2007 | Chudik | |
| 2007/0021779 | A1 | 1/2007 | Garvin et al. | |
| 2007/0032800 | A1 | 2/2007 | Ortiz et al. | |
| 2007/0038218 | A1 | 2/2007 | Grevious | |
| 2007/0043371 | A1 | 2/2007 | Teague et al. | |
| 2007/0055249 | A1 | 3/2007 | Jensen et al. | |
| 2007/0055251 | A1 | 3/2007 | Huebner et al. | |
| 2007/0055255 | A1 | 3/2007 | Siegel | |
| 2007/0060922 | A1 | 3/2007 | Dreyfuss | |
| 2007/0067025 | A1 | 3/2007 | Schwartz | |
| 2007/0073307 | A1 | 3/2007 | Scribner et al. | |
| 2007/0078435 | A1 | 4/2007 | Stone et al. | |
| 2007/0083236 | A1 | 4/2007 | Sikora et al. | |
| 2007/0093847 | A1 | 4/2007 | Scribner et al. | |
| 2007/0100350 | A1 | 5/2007 | Deffenbaugh et al. | |
| 2007/0118217 | A1 | 5/2007 | Brulez et al. | |
| 2007/0123883 | A1 | 5/2007 | Ellis et al. | |
| 2007/0142838 | A1 | 6/2007 | Jordan | |
| 2007/0156174 | A1 | 7/2007 | Kaiser et al. | |
| 2007/0162018 | A1 | 7/2007 | Jensen et al. | |
| 2007/0185488 | A1 | 8/2007 | Pohjonen et al. | |
| 2007/0185532 | A1 | 8/2007 | Stone et al. | |
| 2007/0185568 | A1 | 8/2007 | Schwartz | |
| 2007/0191849 | A1* | 8/2007 | ElAttrache et al. | 606/72 |
| 2007/0191853 | A1 | 8/2007 | Stone | |
| 2007/0198036 | A1 | 8/2007 | Sklar et al. | |
| 2007/0219558 | A1* | 9/2007 | Deutsch | 606/72 |
| 2007/0225719 | A1 | 9/2007 | Stone et al. | |
| 2007/0225805 | A1 | 9/2007 | Schmieding | |
| 2007/0233241 | A1 | 10/2007 | Graf et al. | |
| 2007/0239209 | A1 | 10/2007 | Fallman | |
| 2007/0239275 | A1 | 10/2007 | Willobee | |
| 2007/0250163 | A1 | 10/2007 | Cassani | |
| 2007/0260251 | A1 | 11/2007 | Weier et al. | |
| 2007/0260279 | A1 | 11/2007 | Hotter et al. | |
| 2007/0270856 | A1 | 11/2007 | Morales et al. | |
| 2007/0276387 | A1 | 11/2007 | Morales et al. | |
| 2008/0027430 | A1 | 1/2008 | Montgomery et al. | |
| 2008/0027446 | A1 | 1/2008 | Stone et al. | |
| 2008/0033549 | A1 | 2/2008 | Marshall et al. | |
| 2008/0046009 | A1 | 2/2008 | Albertorio et al. | |
| 2008/0051836 | A1* | 2/2008 | Foerster et al. | 606/232 |
| 2008/0065114 | A1* | 3/2008 | Stone et al. | 606/139 |
| 2008/0071299 | A1 | 3/2008 | Allinniemi et al. | |
| 2008/0082101 | A1 | 4/2008 | Reisberg | |
| 2008/0082127 | A1 | 4/2008 | Stone et al. | |
| 2008/0082128 | A1 | 4/2008 | Stone | |
| 2008/0097430 | A1 | 4/2008 | Bernstein et al. | |
| 2008/0119892 | A1 | 5/2008 | Brailovski et al. | |
| 2008/0132753 | A1 | 6/2008 | Goddard | |
| 2008/0132932 | A1 | 6/2008 | Hoeppner et al. | |
| 2008/0132948 | A1 | 6/2008 | Surti et al. | |
| 2008/0133007 | A1 | 6/2008 | Donnelly et al. | |
| 2008/0140092 | A1 | 6/2008 | Stone et al. | |
| 2008/0140093 | A1 | 6/2008 | Stone et al. | |
| 2008/0140128 | A1 | 6/2008 | Smisson et al. | |

(56) References Cited

U.S. PATENT DOCUMENTS

| | | |
|---|---|---|
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105754 A1 | 4/2009 | Sethi |
| 2009/0118774 A1 | 5/2009 | Miller III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle,, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0046733 A1 | 2/2011 | Eggli |
| 2011/0087284 A1 | 4/2011 | Stone et al. |
| 2011/0106153 A1 | 5/2011 | Stone et al. |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0245585 A1 | 9/2012 | Kaiser et al. |
| 2012/0296427 A1 | 11/2012 | Conner et al. |
| 2012/0310245 A1 | 12/2012 | Hoeppner et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0103082 A1 | 4/2013 | Kaiser et al. |
| 2013/0110251 A1 | 5/2013 | Metzger et al. |
| 2013/0116730 A1 | 5/2013 | Denham et al. |
| 2013/0123813 A1 | 5/2013 | Stone et al. |

FOREIGN PATENT DOCUMENTS

| | | |
|---|---|---|
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| DE | 20207781 U1 | 8/2002 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |

(56) References Cited

FOREIGN PATENT DOCUMENTS

| | | |
|---|---|---|
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 2238944 A2 | 10/2010 |
| EP | 2544607 A1 | 1/2013 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2006023661 A2 | 3/2006 |
| WO | WO-2006055823 A2 | 5/2006 |
| WO | WO-2007045460 A2 | 4/2007 |
| WO | WO-2007109280 A2 | 9/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |

OTHER PUBLICATIONS

Pioneer® Sternal Cable System (2010).
Rapid Sternal Closure (2006) KLS Martin L.P. http://www.rapidsternalclosure.com/medical/demo.php Web accessed Sep. 8, 2008.
Saxena, Pankaj, MCh, DNB et al., "Use of Double Wires in Sternal Closure, A Useful Technique," Texas Heart® Institute. Journal List<Tex Heart Inst J < v.33(4); (2006).
Zeitani, Jacob, M.D., "A New Sternal Reinforcement Device to Prevent and Treat Sternal Dehiscence," CTSNet.org (Jun. 30, 2008).
"AperFix® System Surgical Technique Guide. Single Tunnel Double Bundle. ™" Cayenne Medical brochure. (Aug. 2008) 8 sheets.
"Bio-lntrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of InfraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . ." Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library.

(56) References Cited

OTHER PUBLICATIONS

F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 (Oct.), 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Invitation to Pay Additional Fees mailed Jul. 19, 2012, for PCT/US2012/037703 claiming benefit of U.S. Appl. No. 13/109,667, filed May 7, 2011.
International Preliminary Report on Patentability mailed Sep. 20, 2012 for PCT/US2011/026349 which claims benefit of U.S. Appl. No. 12/719,337, filed Mar. 8, 2010.
International Preliminary Report on Patentability mailed Dec. 6, 2012 for PCT/US2011/038188 claiming benefit of U.S. Appl. No. 12/788,966, filed May 27, 2010.
"Suture Tensioner w/Tensiometer," Arthrex®, Inc. catalog "Next Generation in Knee Ligament Reconstruction & Repair Technology," 2009.
"TriTis™ Tibial Fixation System and Implant" brochure. Scandius Biomedical (2006).
International Search Report and Written Opinion mailed Sep. 21, 2012 for PCT/US2012/037703 filed May 14, 2012 claiming benefit of U.S. Appl. No. 13/109667, filed May 17, 2011 and U.S. Appl. No. 13/109,672, filed May 17, 2011.
US 6,238,418, 05/2001, Schwartz et al. (withdrawn)

\* cited by examiner

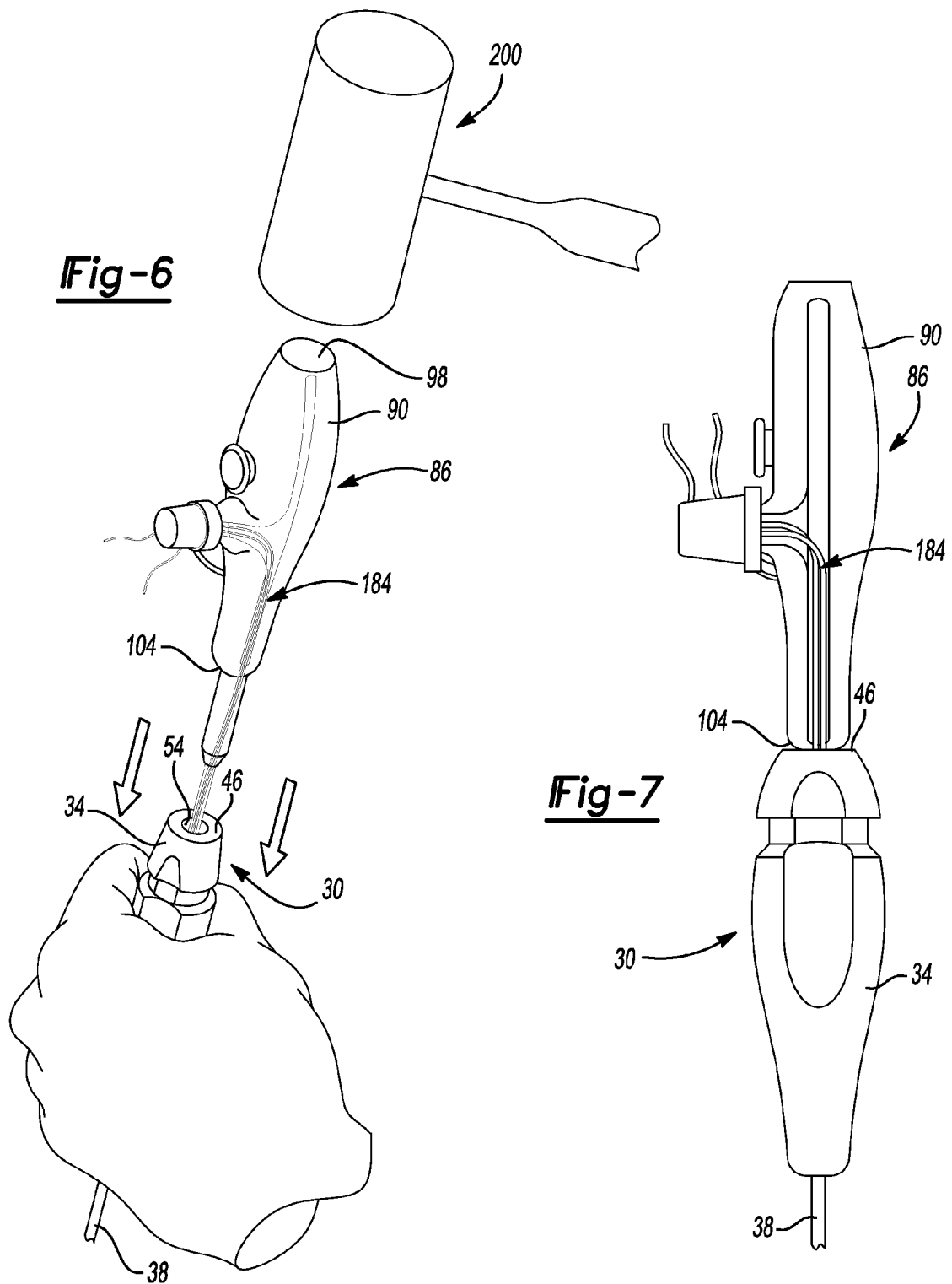

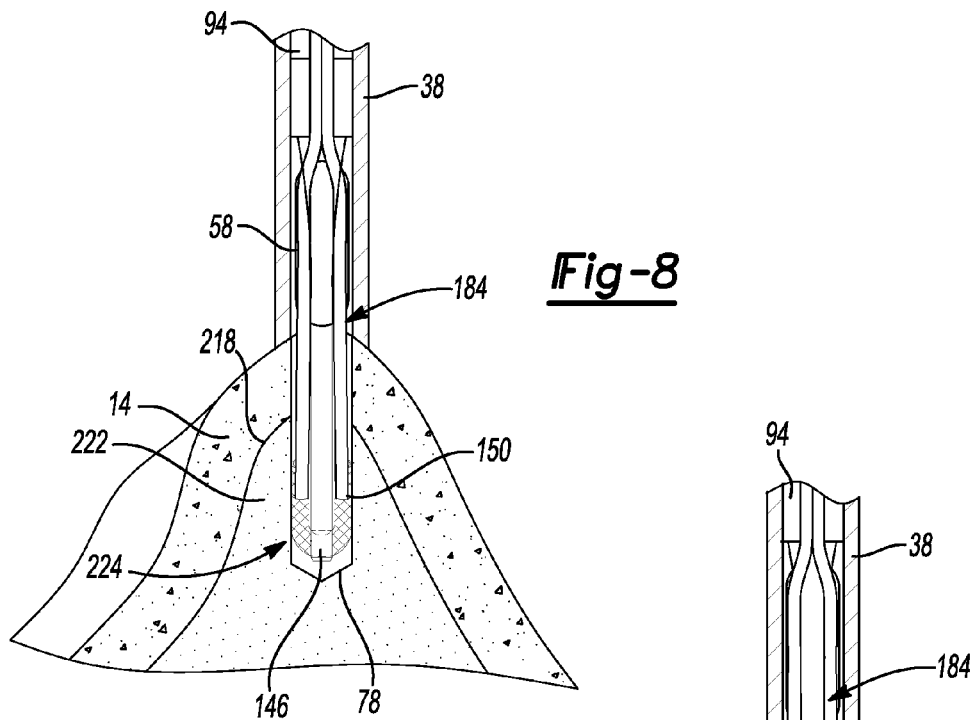
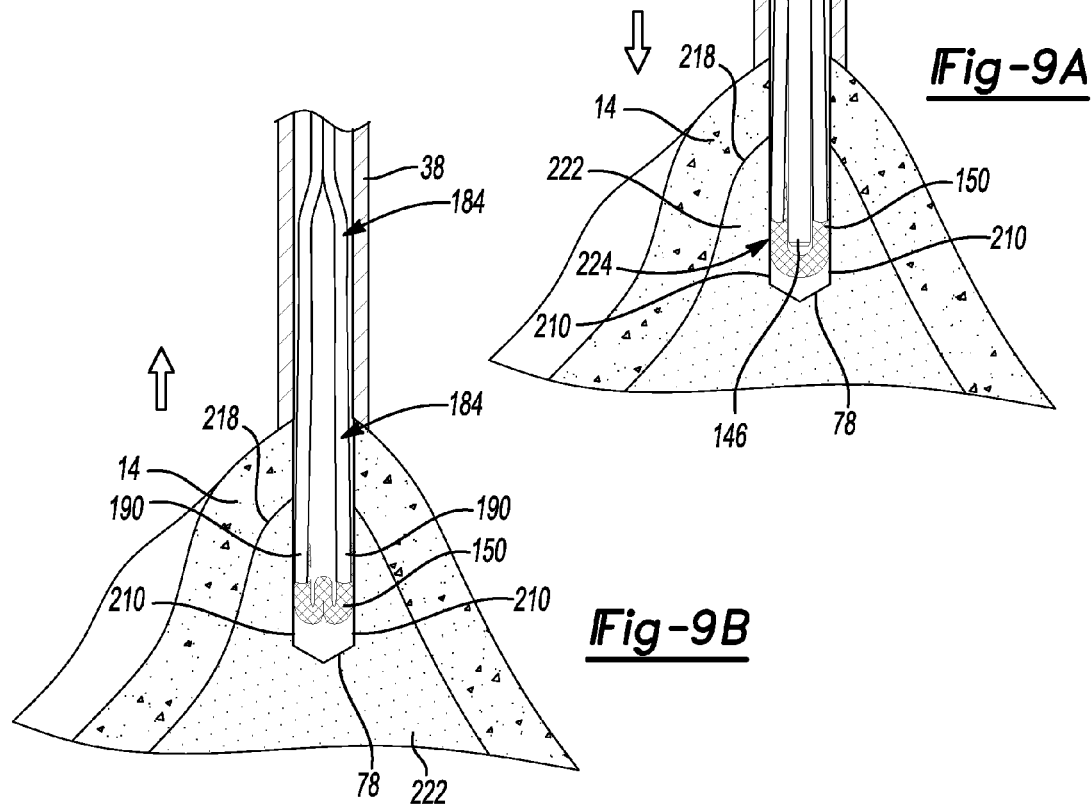
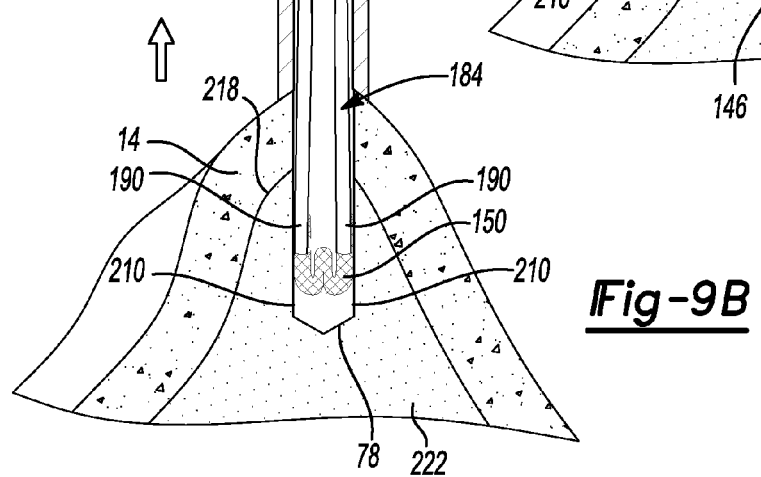

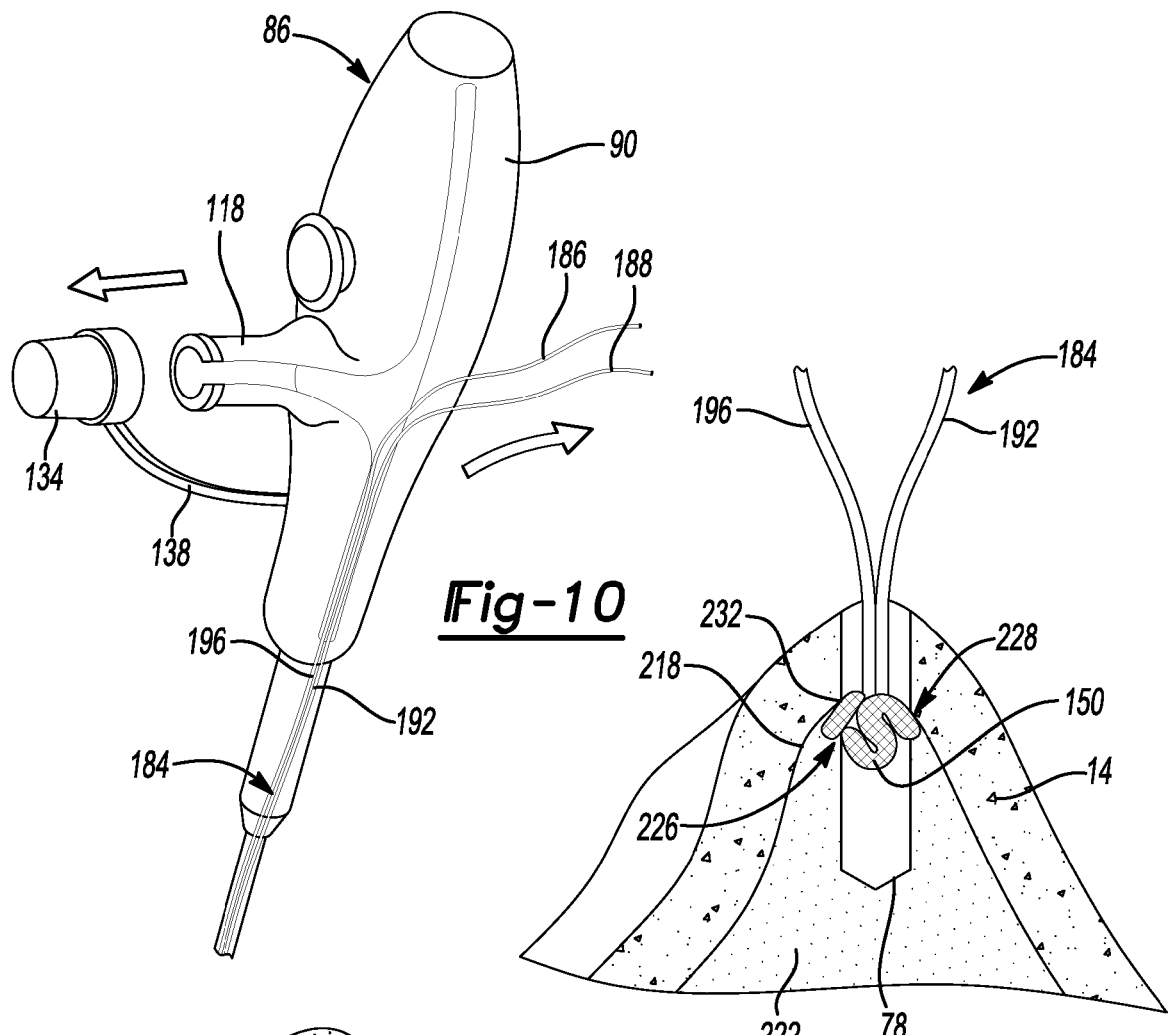
*Fig-10*
*Fig-11*
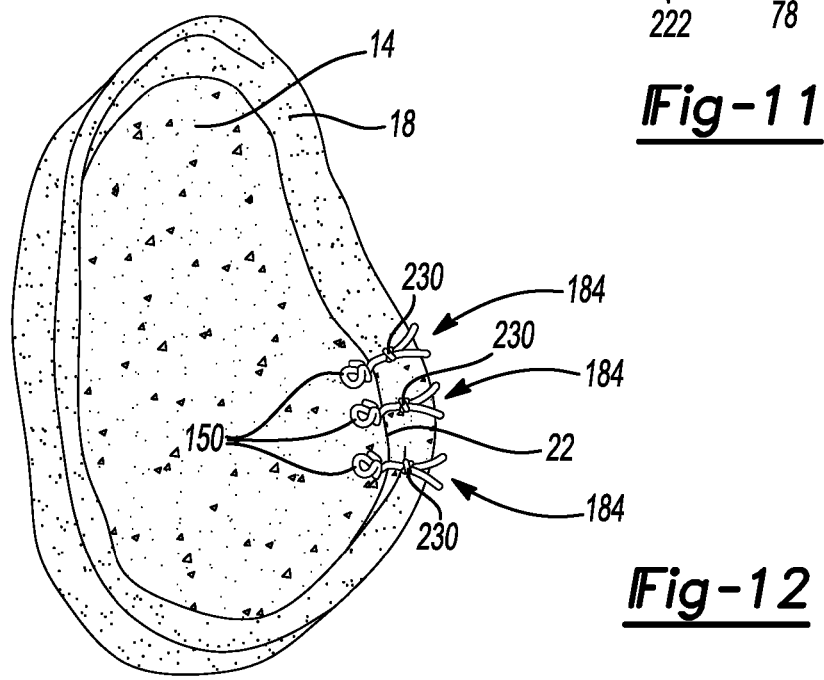
*Fig-12*

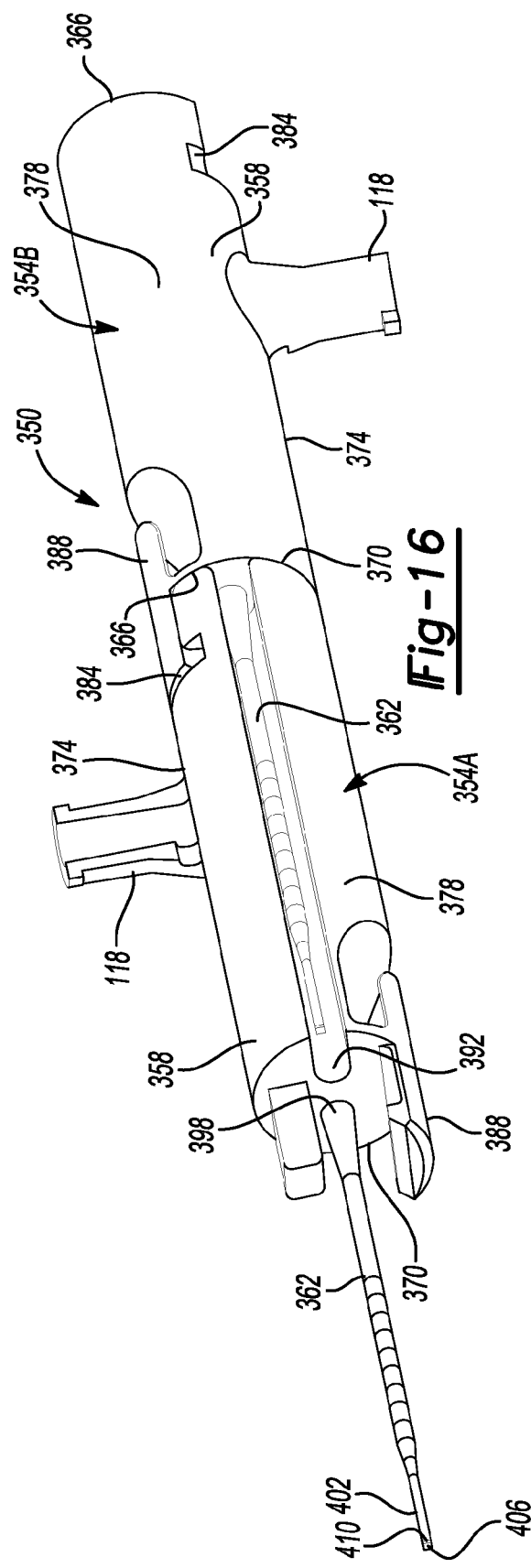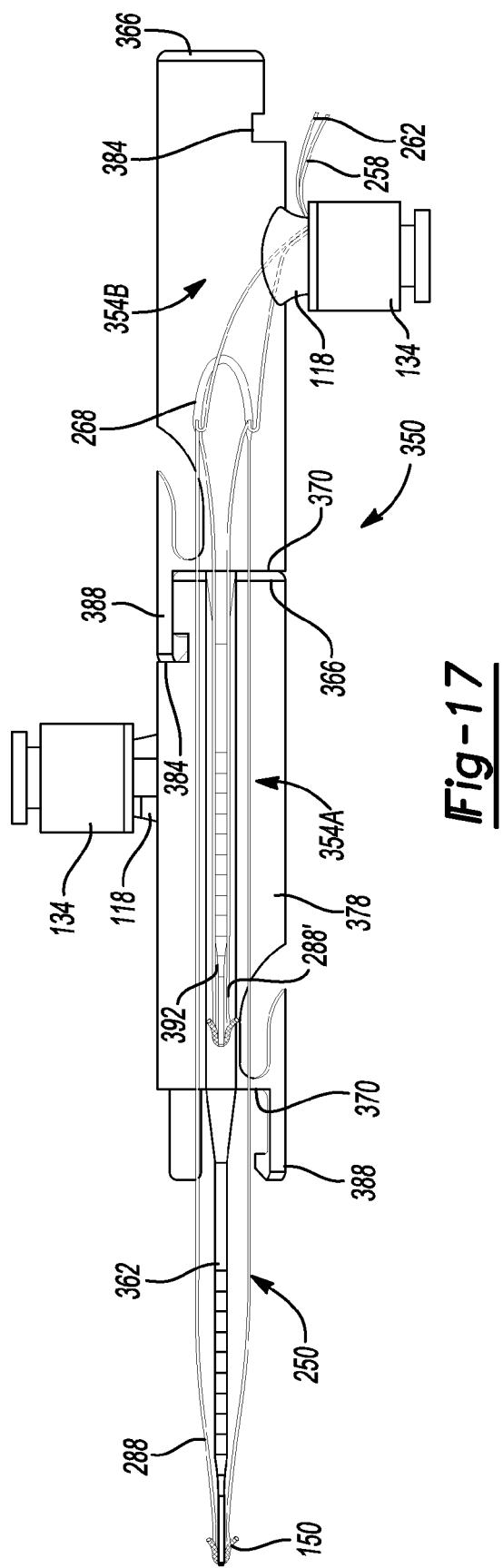

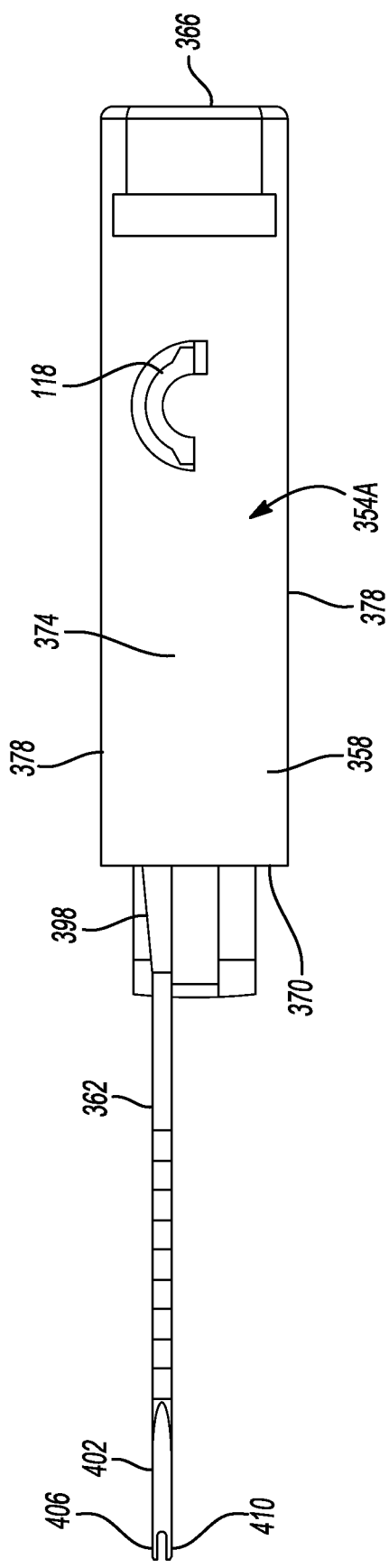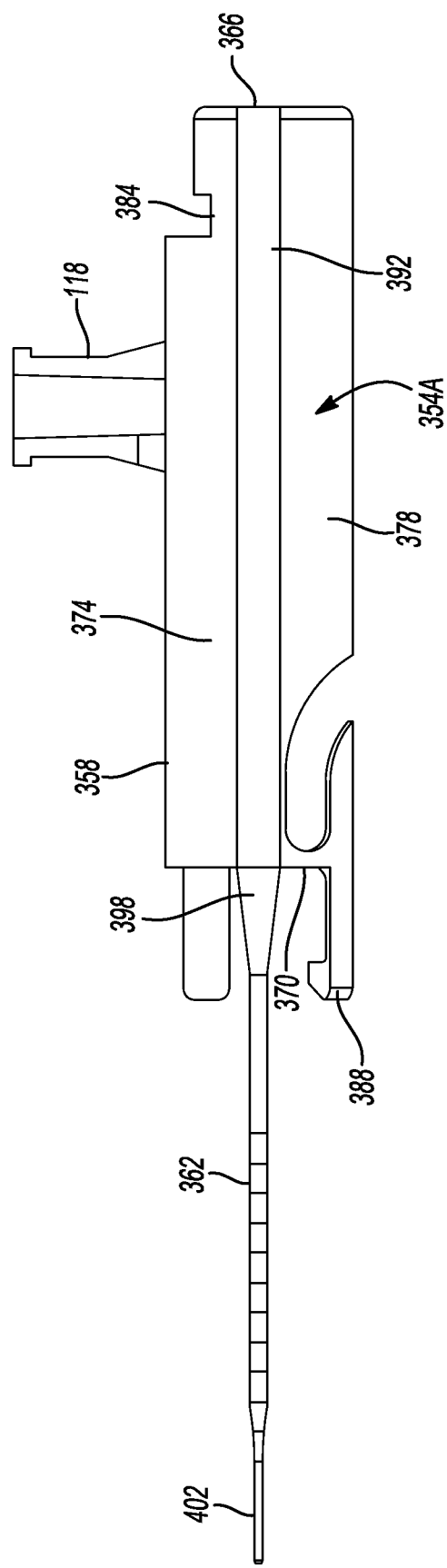

METHOD AND APPARATUS FOR SECURING SOFT TISSUE TO BONE

CROSS-RELATED APPLICATIONS

This application is a continuation-in-part of U.S. patent application Ser. No. 12/719,337 filed on Mar. 8, 2010, which is a continuation-in-part of U.S. patent application Ser. No. 12/489,168 filed on Jun. 22, 2009, which is a continuation-in-part of U.S. patent application Ser. No. 12/474,802 filed on May 29, 2009, which is now U.S. Pat. No. 8,088,130 issued on Jan 3, 2012, which is a continuation-in-part of (a) U.S. patent application Ser. No. 12/196,405 filed on Aug. 22, 2008, which is now U.S. Pat. No. 8,128,658 issued on Mar. 6, 2012; (b) U.S. patent application Ser. No. 12/196,407 filed on Aug. 22, 2008, which is now U.S Pat. No. 8,137,382 issued on Mar. 20, 2012;(c) U.S. patent application Ser. No. 12/196,410 filed on Aug. 22, 2008, which is now U.S. Pat. No 8,118,836 issued Feb. 21,2012; and (d) a continuation-in-part of U.S. patent application Ser. No. 11/541,506 filed on Sep. 29, 2006, which is now U.S. Pat. No. 7,601,165 issued on Oct. 13, 2009.

This application is a continuation-in-part of U.S. patent application Ser. No. 12/570,854 filed on Sep. 30, 2009, which is a continuation-in-part of U.S. patent application Ser. No. 12/014,399 filed on Jan. 15, 2008, which is now U.S. Pat. No. 7,909,851 issued on Mar. 22, 2011.

This application is a continuation-in-part of U.S. patent application Ser. No. 12/702,067 filed on Feb. 8, 2010, which is a continuation of U.S. patent application Ser. No. 11/541,505 filed on Sep. 29, 2006 and is now U.S. Pat. No. 7,658,751 issued on Feb. 9, 2010.

This application is a continuation-in-part of U.S. patent application Ser. No. 12/196,398 filed Aug. 22, 2008, which is now U.S. Pat. No. 7,959,650 issued on Jun. 14, 2011, which is a continuation-in-part of U.S. patent application Ser. No. 11/784,821 filed Apr. 10, 2007.

The disclosures of all of the above applications are incorporated by reference herein.

FIELD

The present disclosure relates generally to a method and apparatus for attaching soft tissue to bone.

BACKGROUND

The statements in this section merely provide background information related to the present disclosure and may not constitute prior art.

Tears caused by trauma or disease in soft tissue, such as cartilage, ligament, or muscle, can be repaired by suturing. Various repair techniques and devices have been developed for facilitating suturing that include the use of rigid, non-flexible anchors and that are effective for their intended purposes. Nevertheless, there is still a need in the relevant art for tissue repair techniques and associated devices for facilitating suturing without requiring the use of rigid anchors.

SUMMARY

This section provides a general summary of the disclosure, and is not a comprehensive disclosure of its full scope or all of its features.

In one form, the present disclosure provides a method for securing soft tissue to bone. The method can include forming a bore in the bone and carrying a flexible anchor into the bore. The flexible anchor can include a passage and can be coupled to a suture construct. The suture construct can include at least one self-locking adjustable loop, and the flexible anchor can include a first profile while being carried into the bore. The method can close include changing a shape of the flexible anchor from the first profile to a second profile forming an anchoring mass to retain the flexible anchor in the bore. Tension can be applied to a portion of the suture construct to reduce a size of the self-locking adjustable loop and secure the soft tissue relative to the flexible anchor and the bone.

In another form, the present disclosure provides a method for securing soft tissue to bone. The method can include forming a bore in the bone and forming a suture construct. Forming the suture construct can include providing a suture having a first and second free ends and a body defining a passage portion; providing first and second flexible suture anchors each having a passage; coupling the first and second anchors to the suture by passing a portion of the suture through a portion of the passage of each flexible anchor; and passing the first and second free ends of the suture into and through the passage portion in opposite directions to form first and second self-locking adjustable loops. The method can also include carrying the first flexible suture anchor into the bore where the flexible anchor includes a first profile while being carried into the bore, and changing a shape of the first flexible anchor from the first profile to a second profile forming an anchoring mass to retain the flexible anchor in the bore. Tension can be applied to the first and second ends of the suture construct to reduce a size of the first and second self-locking adjustable loops and secure the soft tissue relative to the first flexible anchor and the bone.

In yet another form, the present disclosure provides an assembly for securing soft tissue to bone. The assembly can include a flexible tubular anchor having a passage and a flexible member construct. The flexible member construct can include a body defining a passage portion between first and second ends, where the first end can be passed though a portion of the passage of the flexible tubular anchor that is spaced apart from respective ends of the flexible anchor. The first end can also be passed into and through the passage portion via first and second openings associated with the passage portion to form at least one adjustable, self-locking loop. The flexible anchor can be slidably coupled to the flexible member construct and can be configured to be collapsible upon engagement with bone to form an anchoring mass having a locking profile.

Further areas of applicability will become apparent from the description provided herein. It should be understood that the description and specific examples are intended for purposes of illustration only and are not intended to limit the scope of the present disclosure.

DRAWINGS

The present disclosure will become more fully understood from the detailed description, the appended claims and the following drawings. The drawings are for illustrative purposes only and are not intended to limit the scope of the present disclosure.

FIG. 6 is a perspective view of the exemplary surgical technique depicting the inserter slidably positioned in the guide instrument and impacted to drive the flexible anchor into a bore drilled in the glenoid bone;

FIG. 7 is a partial side view of the exemplary surgical technique, inserter and guide instrument of FIG. 6;

FIG. 8 is a partial sectional view of the exemplary surgical technique, inserter and guide instrument of FIG. 6 showing the flexible anchor driven into a bore drilled in the glenoid bone;

FIGS. 9A and 9B are sectional views of the exemplary surgical technique depicting the flexible anchor being deployed from the inserter according to the present disclosure;

FIG. 10 is a partial perspective view of the exemplary surgical technique depicting portions of the suture being decoupled from the inserter according to the present disclosure;

FIG. 11 is a sectional view of the exemplary surgical technique depicting portions of the suture being pulled or tightened to secure the flexible anchor in the bore according to the present disclosure;

FIG. 12 is a perspective view of the exemplary surgical technique depicting multiple anchors being used to secure the labral tear using a sliding knot according to the present disclosure;

FIG. 16 is a perspective view of an exemplary alternative inserter instrument according to the present disclosure;

FIG. 17 is a side view of the inserter of FIG. 16 with an exemplary suture construct coupled thereto according to the present disclosure;

FIG. 18 is a top view of a portion of the inserter of FIG. 16 according to the present disclosure;

FIG. 19 is a side view of the portion of the inserter of FIG. 18 according to the present disclosure;

DETAILED DESCRIPTION

Figure 1:
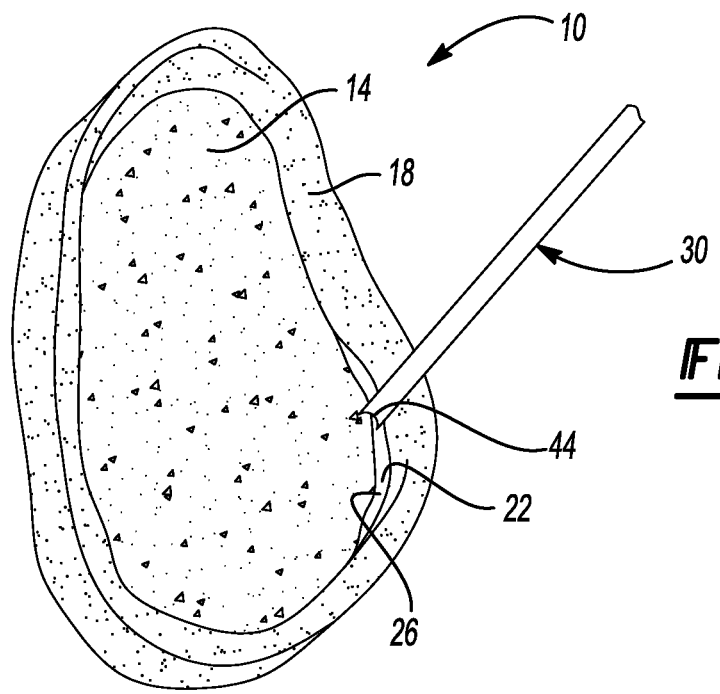
FIG. 1 is a perspective view of an exemplary shoulder labral tear and a partial view of an exemplary guide instrument according to the present disclosure.

The following description is merely exemplary in nature and is not intended to limit the present disclosure, its application, or uses. It should be understood that throughout the drawings, corresponding reference numerals indicate like or corresponding parts and features. Although the following description is related generally to instruments, sutures and suture constructs using flexible anchors in connection with a shoulder labral repair technique, it will be understood that the devices and methods discussed herein can also be applicable to other appropriate surgical procedures, such as, for example, a facelift procedure or a labral tear in a hip joint. Therefore, it will be understood that the following discussions are not intended to limit the scope of the present teachings or claims herein.

With initial reference to FIGS. 1-12, various methods and apparatus are disclosed according to the present teachings for attaching soft tissue to bone, and more particularly for treating a labral tear associated with a shoulder joint. With particular reference to FIG. 1, a portion of an exemplary shoulder joint 10 is shown with a glenoid 14 and a labrum 18 attached thereto. The illustrated shoulder joint 10 includes an exemplary labral tear 22, such as a Bankart labral tear, where a portion of the labrum 18 has been separated from a surface 26 of the glenoid 14.

Continuing with FIGS. 2-12, an exemplary method of repairing labral tear 22 along with exemplary instruments and suture constructs will now be discussed. Once the labral tear 22 has been identified, the portion of the labrum 18 associated with labral tear 22 can be held away or positioned offset from the glenoid surface 26 to expose the underlying bone surface where the labrum 18 will be attached. The bone surface can be prepared as bleeding bone surface with any appropriate tool, such as a rasp (not shown). The labrum 18 can be held away from surface 26 with a guide instrument 30 (FIGS. 2 and 3) or any other appropriate instrument. Guide instrument 30 can include a proximal handle 34 and an elongated cannulated guide member 38 extending from handle 34 to a distal tip 42. The handle 34 can include a first end 46, a second opposite end 50 and an internal bore 54 aligned with guide member 38. Guide member 38 can be configured to guide a drill bit and inserter instrument, as will be discussed herein. A sight window 58 can be provided in a distal end 62 of the guide member 38 adjacent the distal tip 42, as shown for example in FIG. 3.

Figure 2:
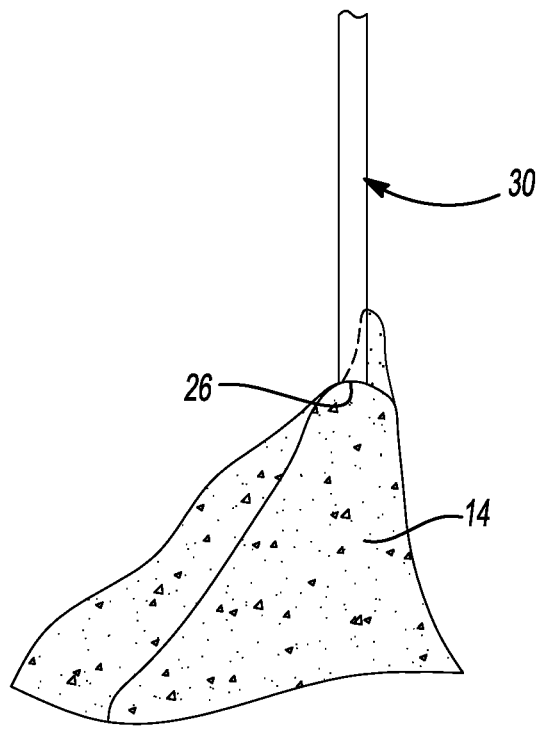
FIG. 2 is an exemplary view of a portion of the glenoid bone with the torn labrum shifted away from a rim of the glenoid by a portion of the exemplary guide instrument according to the present disclosure.
Figure 3:
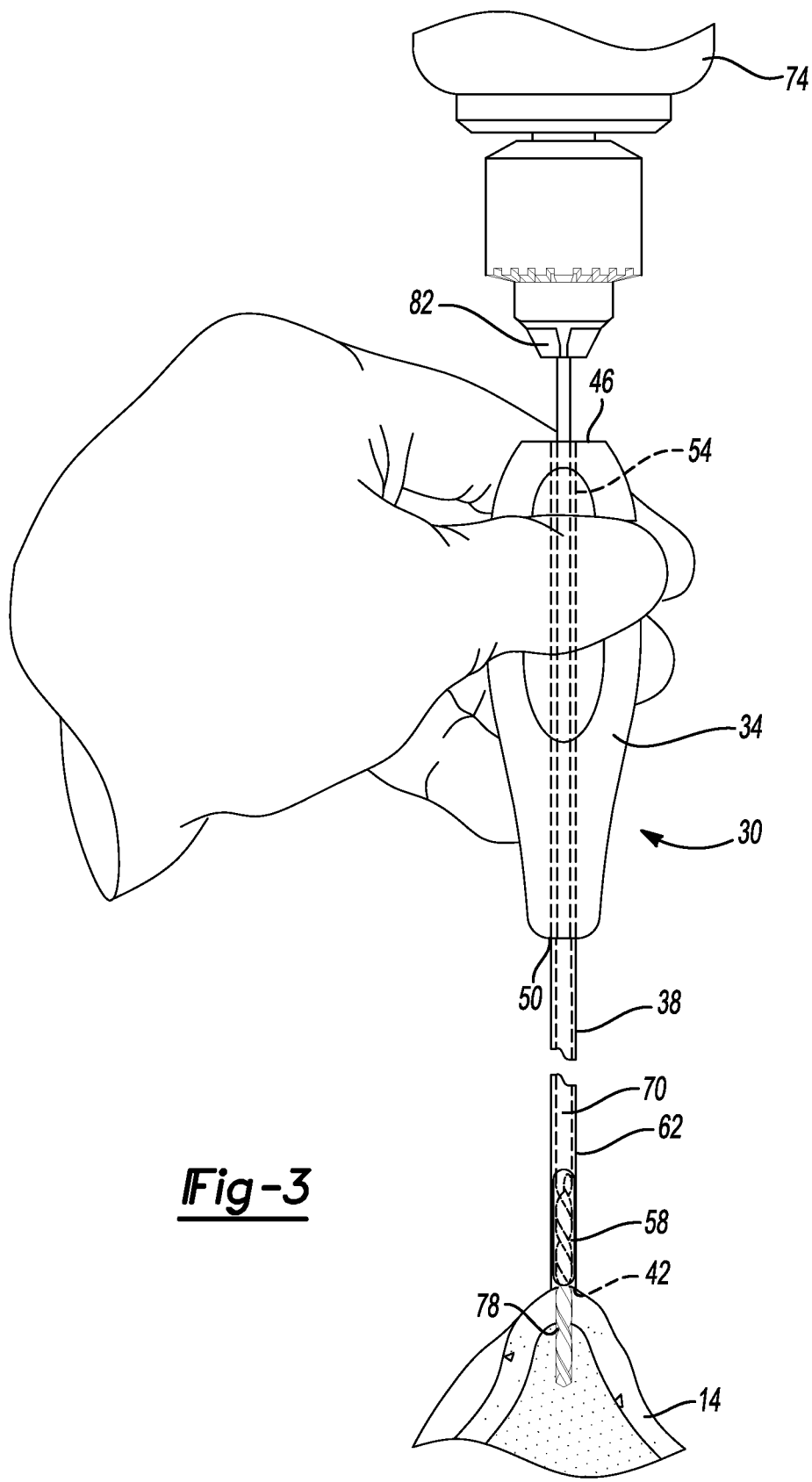
FIG. 3 is a view, partially in section, of an exemplary labral repair surgical technique using the exemplary guide instrument and an exemplary drill.

The distal tip 42 of guide 30 can be positioned on prepared surface 26, as generally shown in FIGS. 2 and 3. Distal tip 42 can include a recess or U-shaped configuration 44 (FIG. 1) to aid in preventing slipping relative to the bone. Once positioned, a drill bit 70 coupled to a drill or driver 74 can be inserted into cannulated guide member 38 to drill a bore 78 in the glenoid bone 14 for receipt of a flexible anchor, as will be discussed in greater detail below. Drill bit 70 can be appropriately sized relative to a length of guide 30 so that a specific length bore can be drilled into the glenoid 14. In particular, the drill can be advanced relative to guide 30 until a chuck or collar 82 of drill 74 contacts first end 46 of handle 34. In this regard, various drill bits having different lengths can be provided for selection by a surgeon to drill an appropriate length bore in the glenoid of a patient. Upon drilling bore 78, drill 74 and bit 70 can be removed from guide 30 while maintaining guide 30 in the same position over bore 78.

Figure 4:
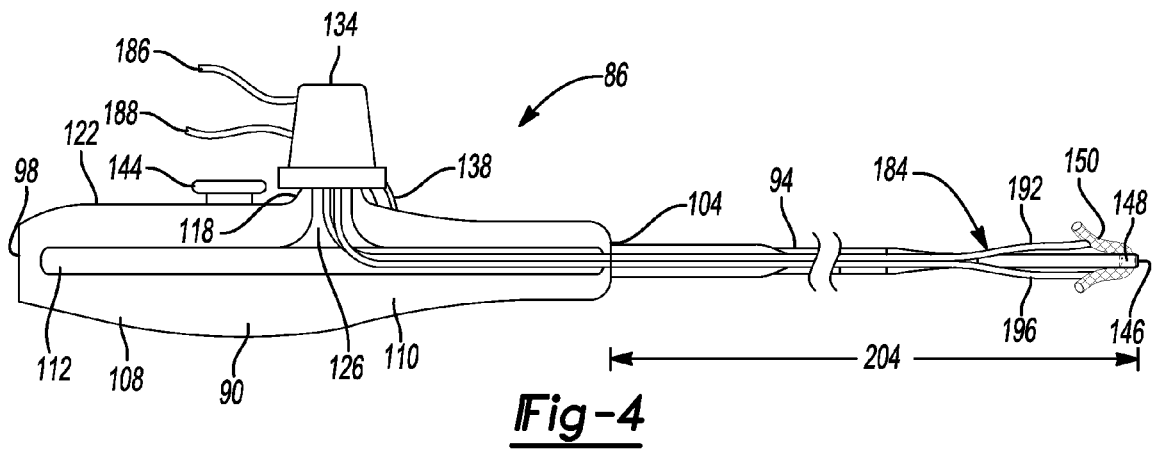
FIG. 4 is a side view of an exemplary inserter instrument with an exemplary suture and flexible anchor coupled thereto according to the present disclosure.

Referring to FIG. 4, an exemplary inserter instrument 86 can be provided to facilitate implanting various suture constructs into a prepared bore in the anatomy, such as bore 78. Inserter 86 can include a handle 90 and an elongate inserter member 94 extending therefrom along a longitudinal axis of the instrument. Handle 90 can include a first end 98, a second end 104 and lateral sides 108. One or both lateral sides 108 can include a longitudinal recess or channel 112 extending along at least a portion of a longitudinal length of handle 90, as also shown in FIG. 4. A protrusion 118 can extend vertically from a top surface 122 of handle 90 or perpendicular to the longitudinal axis and can include a slot or opening 126 on a side 110 of handle 90 having longitudinal channel 112, which slot 126 communicates with channel 112. A cap or securing member 134 can be coupled to handle 90 via strap 138 and can be configured to removably engage protrusion 118 to secure a suture construct to the handle, as will be discussed herein. Handle 90 can also include an appropriately sized projection 144 to facilitate removably coupling securing member 134 to handle 90 when the securing member is not coupled to protrusion 118. In other words, securing member 134 can be pressed onto projection 144 to retain the securing member against handle 90 when not coupled to protrusion 118. In one exemplary configuration, such as the configuration shown in FIG. 4, the protrusion 118 and securing member 134 can include a Luer Lock arrangement or other quick release coupling arrangements.

Figure 5:
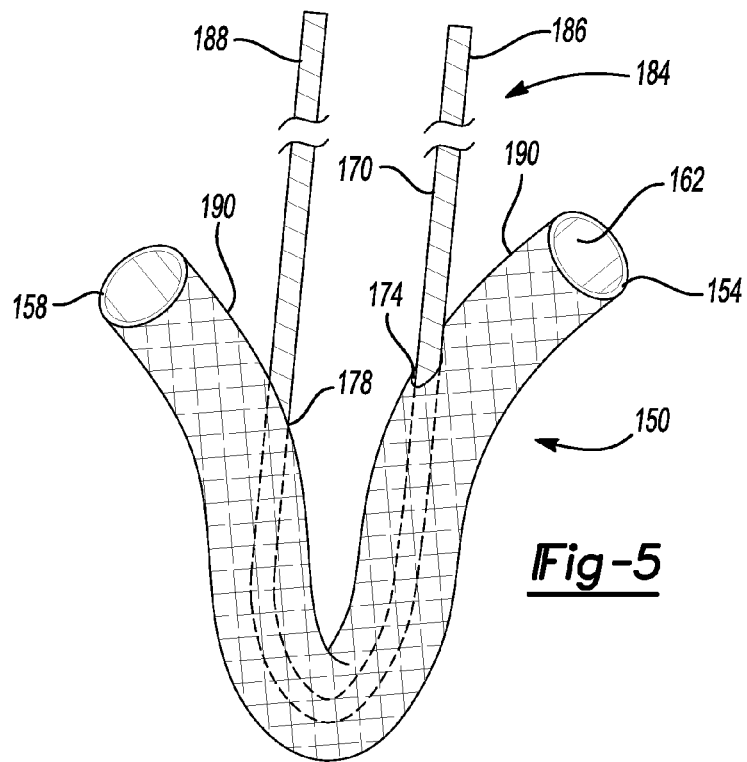
FIG. 5 is a perspective view of an exemplary flexible anchor slidably coupled to a suture according to the present disclosure.

Elongate member 94 can extend from second end 104 and can include a terminal or distal tip 146 having a forked configuration 148 sized and shaped to removably receive a flexible anchor 150, as shown in FIG. 4. Flexible anchor 150 can be an elongate member having a sleeve or tubular configuration with first and second ends 154, 158 and an internal passage 162 extending therebetween, as shown in FIG. 5. The flexible anchor 150 can be made of resorbable or non-resorbable materials, including braided suture, sponges and sponge-like materials in solid form, perforated materials, woven/braided from biocompatible materials or fibers, such as, for example, polymer, polyester, polyethylene, cotton, silk, or other natural or synthetic materials.

The flexible anchor 150 can have any properties that allow the flexible anchor 150 to change shape. In this regard, the flexible anchor 150 can be, for example, compliant, flexible, foldable, squashable, squeezable, deformable, limp, flaccid, elastic, low-modulus, soft, spongy or perforated, or have any other characteristic property that allows it to change shape. In some aspects, the flexible anchor 150 can be coated with biological or biocompatible coatings, and also can be soaked in platelets and other biologics, which can be easily absorbed by the flexible anchor 150. In one exemplary configuration, the flexible anchor 150 can be formed from a strand of No. 5 braided polyester suture. In other words, multiple fibers can be braided together to form a hollow braided suture having a longitudinal passage.

As shown for example in FIG. 5, a suture 170 can be passed through a first opening 174 in a wall of the flexible anchor 150, guided into and along the passage 162, and passed out of the passage 162 through a second opening 178 in a wall of the flexible anchor 150 to form a suture construct 184 having free ends 186 and 188. The openings 174, 178 can be positioned intermediately between the first and second ends 154, 158 of the flexible anchor 150 at a distance of, for example, one-quarter length from ends 154, 158. It will be appreciated that the openings 174, 178 can be apertures or voids in the woven fabric of the flexible anchor 150, such that the openings 174, 178 do not disrupt or break the weave of the flexible anchor 150 when made of braided or woven material. Further, portions of the flexible anchor 150 between the first and second ends 154, 158 and the corresponding first and second openings 174, 178, can define anchoring leg or tail portions 190 that can provide additional resistance for securing the flexible anchor 150 relative to the bone, as will be discussed in greater detail herein. In one exemplary configuration, suture 170 can pass only through openings 174, 178 and a portion of the passage 162 extending therebetween to form a loop that does not extend through tail portions 190.

Suture construct 184 can be loaded onto inserter 86 by coupling flexible anchor 150 to the forked configuration 148, as shown in FIG. 4. First and second portions 192, 196 of suture construct 184 can be routed along elongate member 94 and into longitudinal channel 112. Suture portions 192, 196 can then be routed into protrusion 118 via slot 126 and secured thereto with securing member 134, as also shown in FIG. 4. In one exemplary configuration, free ends 186, 188 of suture portions 192, 196 can extend from protrusion 118.

With suture construct 184 coupled to inserter 86, the elongate member 94 of inserter 86 can be inserted into guide 30 to position flexible anchor 150 in prepared bore 78, as shown in FIGS. 6, 7 and 8. The flexible anchor 150 can include a first profile or shape 224 that allows for insertion through guide 30 and into prepared bore 78. A mallet or other impacting instrument 200, as shown in FIG. 6, can be used to impact the first end 98 of inserter 86 to fully seat flexible anchor 150 in bore 78, as shown in FIG. 8. In one exemplary configuration, the elongate member 94 of inserter 86 can include a specific length 204, as indicated in FIG. 4, calibrated to a length of guide 30 and drill bit 70 such that a user can advance the inserter 86 until the second end 104 of the inserter handle 90 contacts the first end 46 of guide member handle 34, as shown in FIG. 7. Alternatively, the user can observe the sight window 58 to determine initial placement of the soft anchor in bore 78, as also shown in FIG. 8.

With the flexible anchor fully seated in bore 78, as shown in FIG. 8, the inserter 86 can be slightly moved or withdrawn in an axial direction relative to bore 78 to deploy the flexible anchor 150 from the elongate member 94 of inserter 86, as shown in FIGS. 9A and 9B. During the axial translation, the tail portions 190 can facilitate frictional engagement with sidewalls 210 of bore 78 to aid in deploying flexible anchor 150 from inserter 86. Upon deployment of flexible anchor 150, the securing member 134 can be removed from protrusion 118 and the suture portions 192, 196 can be released from inserter handle 90, as shown in FIG. 10. Inserter 86 can then be removed from guide 30 and guide 30 can be removed from its position of contact with glenoid surface 26, as shown in FIG. 11. It should be appreciated that inserter 86 and guide 30 can be removed separately as discussed above or, in the alternative, can be removed simultaneously.

As shown in FIG. 11, the free ends 186, 188 of suture construct 184 can be pulled in a direction that is generally coaxial with and away from bore 78 to thereby set the flexible anchor 150 in an anchoring configuration relative to a cortical bone layer 218 of the glenoid 14. In one exemplary configuration, during setting of flexible anchor 150, portions of the anchor, including tail portions 190, can bunch together, collapse, expand and/or change shape to a second shape, configuration or locking profile 226 to form an anchoring mass 228, as shown in FIG. 11. Anchoring mass 228 can then be set or seated against an inner face of cortical bone layer 218 surrounding bore 78. In an exemplary configuration, second shape or profile 226 can include a width that is greater than that of first profile 224 and that of the initially formed bore 78 such that portions of flexible anchor 150 can expand into the cancellous bone layer 222 and extend transversely beyond the width or diameter of bore 78 beneath the cortical bone 218. For example, the anchoring mass 228 can include a width in a direction perpendicular to a longitudinal axis of bore 78 greater than the width of first profile 224 and the width of initially formed bore 78. In an exemplary configuration, the flexible anchor 150 can lock against a ledge 232 of cortical bone layer 218, as shown in FIG. 11.

In one exemplary configuration, flexible anchor 150 can include an outer diameter of 1.4 mm in cross-section and can be inserted and set into a 1.4 mm diameter bore 78. With the flexible anchor 150 folded about an axis transverse thereto and coupled approximately mid-length to forked configuration 148 of distal tip 146 of inserter elongate member 94, a slight impacting action on inserter instrument 86 may be required to fully insert anchor 150 in bore 78, as discussed above. Flexible anchor 150 can provide pull-out strength at least equivalent to that of conventional non-suture formed hard anchors that require a significantly larger bore in the bone. For example, flexible anchor 150 having a 1.4 mm diameter and being formed of polyester suture can have an equivalent or greater pull-out force than a conventional hard anchor having a 3 mm diameter and being formed of PEEK, based on static load testing. Thus, it can be seen that flexible anchor 150 provides fixation strength comparable to larger, hard bone anchors while requiring significantly less bone disruption. The flexible nature and smaller size of flexible anchor 150, combined with the corresponding smaller size of bone hole 78, provides an ability to use the suture construct 184 in a less invasive manner as well as in areas of the anatomy where the larger, hard anchors cannot be used. It should be appreciated that flexible anchors of varying diameters or widths in cross section can be used, including diameters or widths within a range of 0.3 mm to 3.0 mm, or greater.

With reference to FIG. 12, once the anchor has been set, as discussed above, a sliding knot 230 can be formed to secure the portion of the labrum 18 associated with labral tear 22 to the glenoid 14. In this regard, it will be appreciated that the suture 170 can slide relative to the set anchor 150 in the set configuration of FIG. 11, so as to tightly secure the sliding knot against the labrum, as shown in FIG. 11. In other words, each end 186, 188 of the suture 170 can be moved or slid relative to the set anchor 150. The sliding knot 230 can be formed with one free end 186, 188 knotted about the opposing leg of suture 170 and the other free end 188, 186 of the opposing leg of suture 170 can be pulled or tightened to tightly secure the sliding knot 230 against the labrum 18, as shown in FIG. 12 with reference to FIG. 5. In one exemplary configuration, the free ends of suture 170 can be passed around lateral sides 234 (FIG. 20) of labrum 18 and then the sliding knot 230 can be tied and the suture 170 can be tensioned to tightly secure labrum 18 to glenoid 14 at the area of the prepared bone 26 shown in FIG. 2. In another exemplary configuration, one free end of suture 170 can be passed through a portion of the labrum proximate glenoid surface 26 and the other free end can be passed around a lateral side of the labrum 18. The sliding knot 230 can then be formed and the suture 170 can be tightened to secure labrum 18 to glenoid 14.

Figure 13:
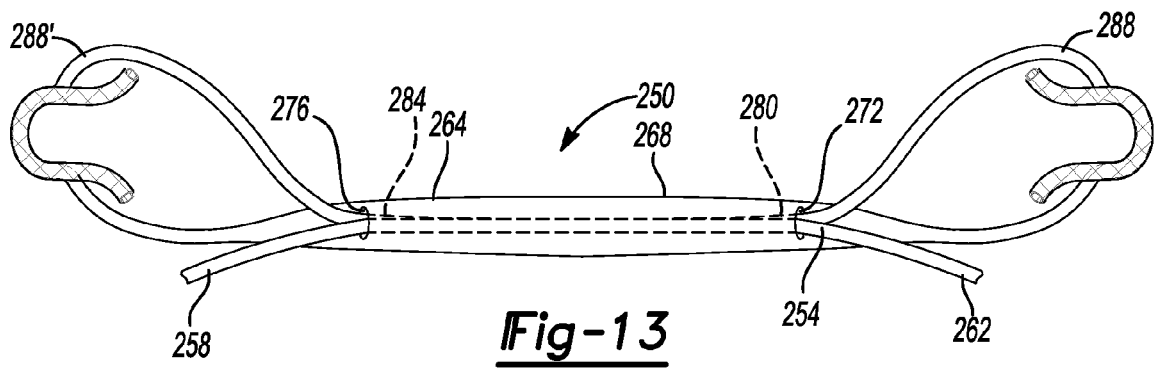
FIGS. 13, 14 and 15 are views of exemplary suture constructs with flexible anchors according to the present disclosure.

Turning now to FIGS. 13-19, exemplary alternative suture constructs and an associated alternative inserter will now be discussed. With particular reference to FIG. 13, a preformed adjustable self-locking suture construct 250 is provided according to the present teachings and can include a braided suture 254 having a first end 258 and a second end 262, and can include a body 264 that defines a longitudinal passage portion 268 therein between first and second ends 258, 262, as shown in FIG. 13. The passage portion 268 can define a pair of apertures 272, 276 at opposed ends thereof. To form construct 250, the first end 258 can be passed through aperture 272 and passage portion 268 and out aperture 276 such that a portion 280 of suture 254 following first end 258 extends through passage portion 268. In a similar manner, second end 262 can be passed through aperture 276 and passage portion 268 and out aperture 272 such that a portion 284 of suture 254 following second end 262 also extends through passage portion 268. This configuration forms two loops 288 and 288', as shown in FIG. 13. It should be appreciated that while passage portion 268 is shown having two apertures or openings 272, 276, passage portion 268 can have additional openings and/or can include additional passage portions.

The pulling or tensioning of ends 258, 262 can cause reciprocal movement of portions 280, 284 relative to passage portion 268, and the loops 288, 288' can be reduced to a desired size placed in a desired tension. Tension in loops 288, 288' can cause the body 264 defining the passage portion 268 to be placed in tension and therefore cause passage portion 268 to constrict about portions 280, 284 passed therethrough. This constriction reduces the diameter of passage portion 268, thus forming a mechanical interface between the exterior surfaces of portions 280, 284 and an interior surface of passage portion 268. This constriction results in static friction between the interior and exterior surfaces at the mechanical interface, causing the adjustable suture construct 250 to "automatically" lock in a reduced size or diameter configuration in which tension is maintained without use of a knot. Adjustable suture construct 250 can include a pair of flexible anchors 150 coupled to loops 288, 288' in a similar manner as discussed above with respect to suture construct 184. Suture construct 250 with adjustable loops 288, 288' can be used to secure the labral tear 22 and/or in other procedures such as a facelift, as will be discussed herein.

Figure 14:
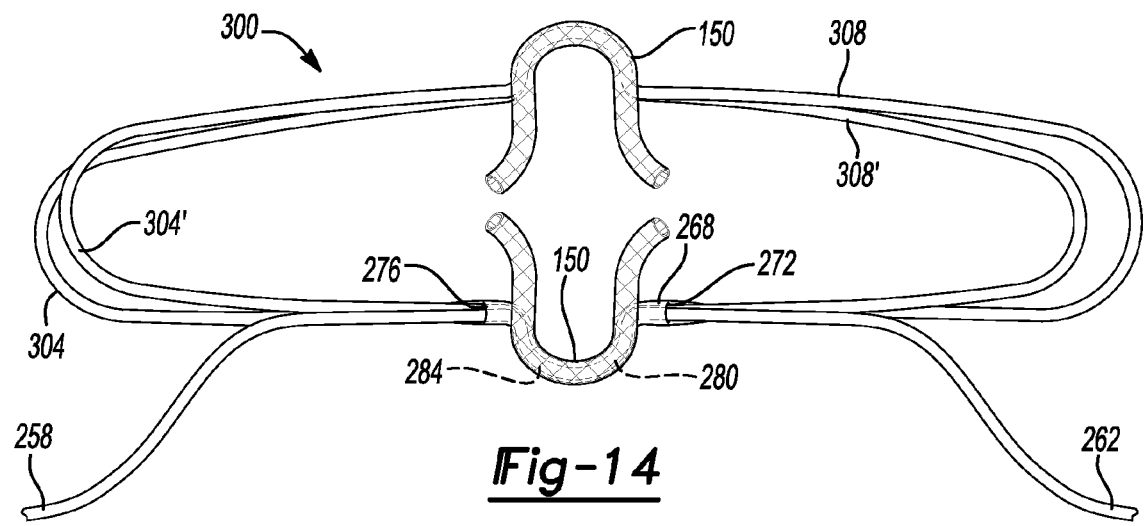

With reference to FIG. 14 and continuing reference to FIG. 13, an alternative preformed adjustable self-locking suture construct 300 is shown. Construct 300 can be preformed to include a double loop configuration having two loops 304, 304' that each traverse a path from one end of passage portion 268 to the other end thereof, instead of each loop being disposed at respective opposite ends of passage portion 268 as in construct 250. Suture construct 300 can be formed by passing the first end 258 of the suture through aperture 276, through passage portion 268 and out aperture 272. The second end 262 can be passed through aperture 272, through the passage portion 268 and out the aperture 276. In various aspects, the first and second apertures 272, 276 can be formed during the braiding process as loose portions between pairs of fibers defining the suture 254, as discussed above.

Passing ends 258, 262 through the apertures 272, 276 can form the loops 304, 304'. The loops 304, 304' can define mount or summit portions 308, 308' of the adjustable suture construct 300 and can be disposed generally opposite from the passage portion 268. Adjustable suture construct 300 can include a pair of flexible anchors 150, as shown in FIG. 14. One flexible anchor 150 can be coupled to the summit portions 308, 308' of loops 304, 304' such that both loops 304, 304' extend the respective flexible anchor 150 in a similar manner as discussed above with respect to suture construct 184. The other flexible anchor can be coupled to passage portion 268 such that passage portion 268 extends through the flexible anchor 150 in a similar manner as discussed above. Suture construct 300 can also be used, for example, to secure the labral tear 22 and/or in other procedures such as a facelift, as will be discussed herein.

The longitudinal and parallel placement of the first and second ends 258 and 262 of the suture 254 within the passage portion 268 resists the reverse relative movement of the first and second portions 280, 284 of the suture construct 300 once it is tightened. The tensioning of the ends 258 and 262 can cause reciprocal movement of the portions 280, 284 relative to passage portion 268. Upon applying tension to the first and second ends 258 and 262, the loops 304, 304' can be reduced to a desired size or placed in a desired tension. Tension in the loops 304, 304' can cause the body of the suture 254 defining the passage portion 268 to be placed in tension and therefore cause passage portion 268 to constrict about the portions 280, 284 similarly to the constriction discussed above with respect to construct 250. This constriction can cause the adjustable suture construct 300 to "automatically" lock in a reduced size or smaller diameter configuration.

Figure 15:
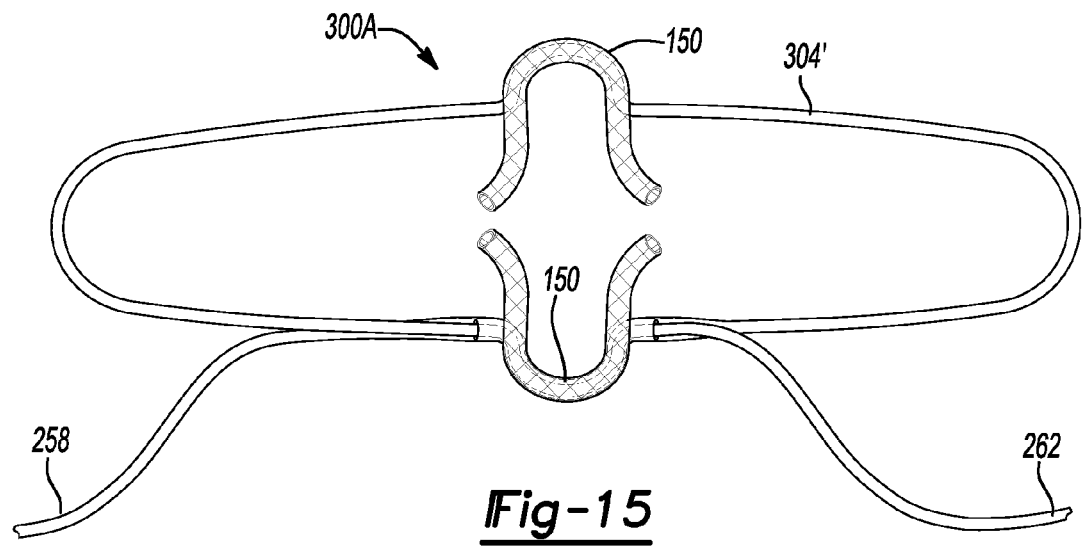

Turning now to FIG. 15, an exemplary adjustable self-locking suture construct 300A is provided having only one loop 304'. Adjustable suture construct 300A can be preformed in a similar manner as construct 300, but with only one loop. Suture construct 300A can include a pair of flexible anchors 150 coupled thereto in a similar manner as discussed above. A further discussion of the suture constructs 250, 300 and 300A are provided in U.S. patent Ser. No. 11/541,506 filed on Sep. 29, 2006 entitled "Method and Apparatus for Forming a Self-Locking Adjustable Suture Loop" assigned to Biomet Sports Medicine, LLC, the disclosure of which is incorporated herein by reference.

Referring now to FIGS. 16-19, an exemplary inserter instrument 350 is provided in accordance with the present teachings and can include a pair of inserters 354A and 354B removably coupled together, as shown in FIG. 16. In one exemplary configuration, each inserter can include the same features and thus the following discussion of the features of inserter 354A will be understood to apply to inserter 354B as well. Inserter 354A can include a handle 358 and an elongate member 362 extending therefrom, as shown in FIGS. 18 and 19. Handle 358 can include a first end 366, a second opposite end 370, a top surface 374, and lateral sides 378. First end 366 can include a female coupling arrangement 384 and second end 370 can include a male coupling arrangement 388. At least one lateral side 378 of handle 358 can include a longitudinal recess or channel 392 configured to receive the elongate member of inserter 354B when coupled thereto, as will be discussed below. Handle 358 can also include protrusion 118 extending from top surface 374 and securing member 134 configured to be coupled thereto, as shown in FIG. 17 and discussed above.

Elongate member 362 can include a first end 398 coupled to the second end of handle 358 and an opposite second end 402 forming a distal tip 406 of inserter 354A. Distal tip 406 can include a forked configuration 410 sized and shaped to receive a flexible anchor 150 similar to inserter 86 discussed above. Elongate member 362 can be coupled to handle 358 in a position laterally offset from a longitudinal center of handle 358, as shown in FIG. 18. Laterally offsetting elongate member 362 provides the ability to removably couple inserters 354A and 354B together in a co-axially aligned fashion, as shown in FIGS. 16 and 17.

To couple inserter 354B to inserter 354A, the second end 370 of handle 358 of inserter 354B can be placed proximate the first end 366 of handle 358 of inserter 354A. Inserter 354B can be orientated such that its longitudinal axis is parallel to the longitudinal axis of inserter 354A and the elongate member of inserter 354B is substantially aligned with the longitudinal channel of inserter 354A, as shown for example in FIGS. 16 and 17. The male coupling arrangement of 354B can then be coupled to the female coupling arrangement of inserter 354A such that the handles of inserters 354A and 354B abut each other and the elongate member 362 of inserter 354B is received in the longitudinal channel 392 of inserter 354A.

One of the exemplary preformed adjustable suture constructs 250, 300, 300A can be coupled to inserter 350 for use in an associated surgical procedure, as will be discussed below. It should be appreciated that other adjustable suture constructs, such as illustrated and disclosed in the applications incorporated by reference herein, can be used with inserter 86 or 350 in various surgical techniques. With particular reference to FIG. 17, one of the flexible anchors 150 can be coupled to the distal tip 406 of inserter 354A and the other flexible anchor can be coupled to the distal tip of inserter 354B. It should be appreciated that the suture constructs can be coupled to inserters 354A and 354B before or after inserters 354A and 354B are coupled together. The loop portions and ends of the suture construct can be routed in various configurations relative to inserters 354A and 354B to removable couple the respective suture construct thereto. In one exemplary configuration, suture construct 250 can be coupled to inserter 350, where the flexible anchor 150 of loop 288 can be coupled to the distal tip 406 of inserter 354A and the flexible anchor 150 of loop 288' is coupled to the distal tip of inserter 354B. The remaining portions of the loops 288, 288' as well as the ends 258, 262 can be coupled to one or both of the protrusions 118. In one exemplary configuration, loops 288, 288' and free ends 258, 262 are coupled to the protrusion of inserter 354B so that the loops and free ends do not have to be decoupled from inserter 354A when inserter 354B is decoupled therefrom, as will be discussed in greater detail below.

Adjustable suture construct 300 can also be used with inserter 350 in a similar manner to adjustable suture construct 250 discussed above. As will be discussed in greater detail below, the flexible anchor 150 coupled to inserter 354A can be implanted into the anatomy before the flexible anchor 150 coupled to inserter 354B. In this regard, and in connection with adjustable suture construct 300, an associated surgical procedure can dictate which flexible anchor 150 should be coupled to each of inserters 354A and 354B. For example, in a surgical procedure where one of the flexible anchors 150 of construct 300 will be implanted into the bone and the other flexible anchor will engage an outer surface of soft tissue, such as the labrum 18, a determination will need to be made whether the flexible anchor 150 on the passage portion 268 will be implanted in the bone or be positioned relative to the outer surface of the soft tissue. If the flexible anchor 150 associated with passage portion 268 is desired to be implanted into the bone, then this flexible anchor 150 should be coupled to inserter 354A and flexible anchor 150 associated with summit portions 308, 308' should be coupled to inserter 354B.

Figure 20:
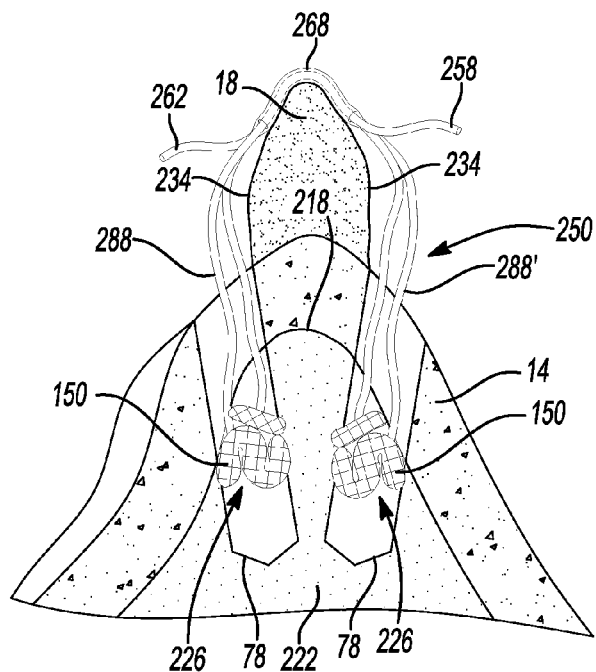
FIG. 20 is a sectional view of an exemplary surgical technique for the shoulder labral tear using an exemplary suture construct positioned over at least a portion of the labrum according to the present disclosure.

With additional reference to FIG. 20, an exemplary surgical technique for securing labral tear 22 or other soft tissue will now be described in greater detail in connection with inserter 350. A pair of bores 78 can be drilled into the glenoid bone 14 adjacent lateral sides of labrum 18 using a similar procedure as discussed above in FIGS. 1-12. Adjustable suture construct 250 can be coupled to inserter 350 as discussed above and the elongate member 362 of inserter 354A can be inserted into a first one of the bores 78 to deploy the flexible anchor 150 associated with loop 288 in the manner discussed above. It should be appreciated that inserter 350 can be used with or without guide 30. With the flexible anchor 150 associated with inserter 354A deployed, inserter 354B can be decoupled from inserter 354A in anticipation of implanting the flexible anchor associated with loop 288' into the second one of the bores 78. If any portions of loops 288, 288' or ends 258, 262 are coupled to the protrusion 118 of inserter 354A, such portions or ends can be released therefrom.

Inserter 354A can be removed from the immediate vicinity of the surgical area and the elongate member 362 of inserter 354B can be inserted into the second one of the bores 78 to position the flexible anchor 150 associated with loop 288' therein. This flexible anchor can be deployed as discussed above and any suture loop portions and/or ends can be decoupled from the protrusion 118. Suture construct 250 can now be positioned such that the construct 250 spans around an exterior surface 418 with the passage portion positioned between the first and second bores 78, as shown in FIG. 20. Tension can be applied to each of the free ends 258, 262 to set the anchors (as discussed above) and secure the labrum 18 to the glenoid 14. It should be appreciated that while the free ends are being tensioned, portions of the loops 288, 288' can slide relative to the set anchors as the self-locking adjustable suture construct 250 is tightly secured against labrum 18 without the use of a knot. In addition, while adjustable suture construct 250 is shown extending around labrum 18, it should be appreciated that portions of suture construct 250 can pierce through lateral sides 234 of labrum 18 proximate bores 78.

Figure 21:
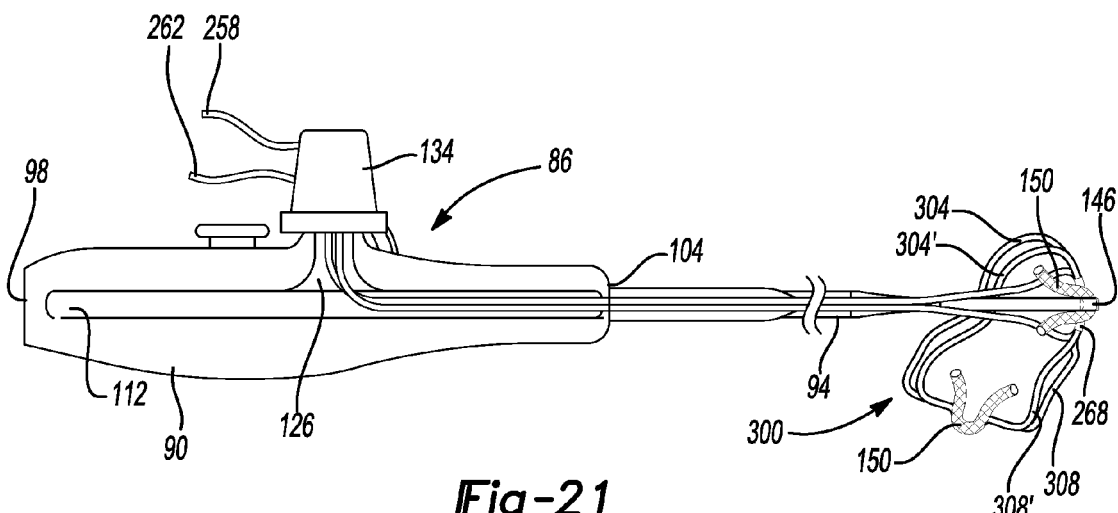
FIG. 21 is a side view of the inserter of FIG. 4 with an exemplary suture construct coupled thereto according to the present disclosure.

Turning now to FIG. 21, inserter 86 is shown having suture construct 300 coupled thereto in place of suture construct 184. In this exemplary configuration, flexible anchor 150 associated with passage portion 268 is coupled to the distal tip 146 of elongate member 94. The second flexible anchor 150 associated with summit portions 308, 308' can extend freely from inserter 86, as shown in FIG. 21. The first and second ends 258, 262 of construct 300 extend along the elongate member 94 into channel 112 and can be secured to protrusion 118 with securing member 134.

Figure 22:
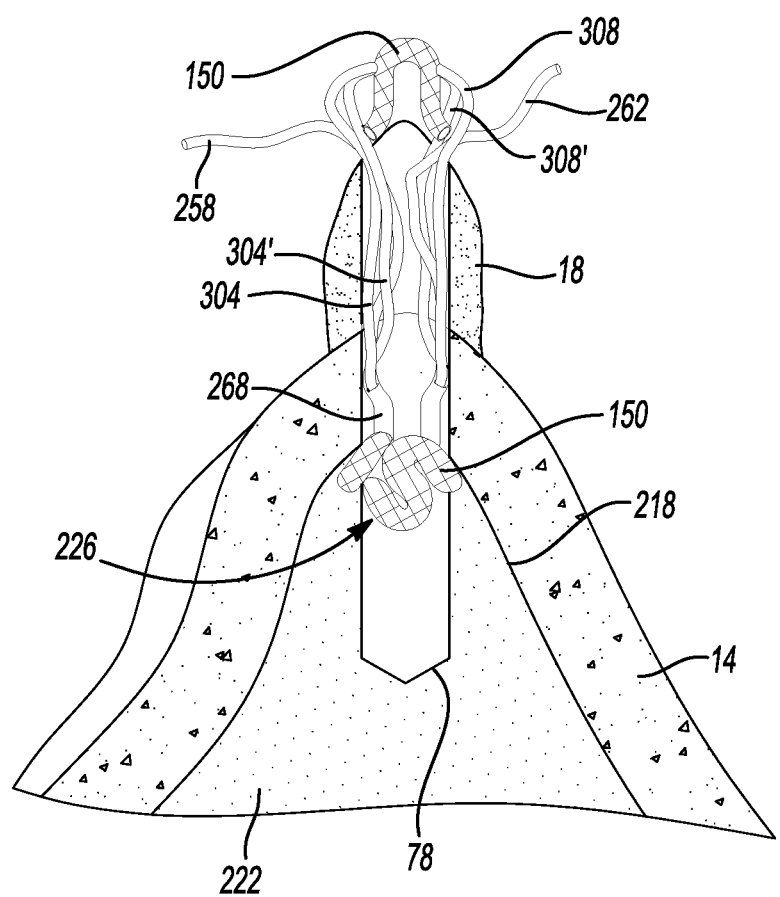
FIG. 22 is a sectional view of an exemplary surgical technique for the shoulder labral tear using an exemplary suture construct extending through a portion of the labrum according to the present disclosure.
Figure 23:
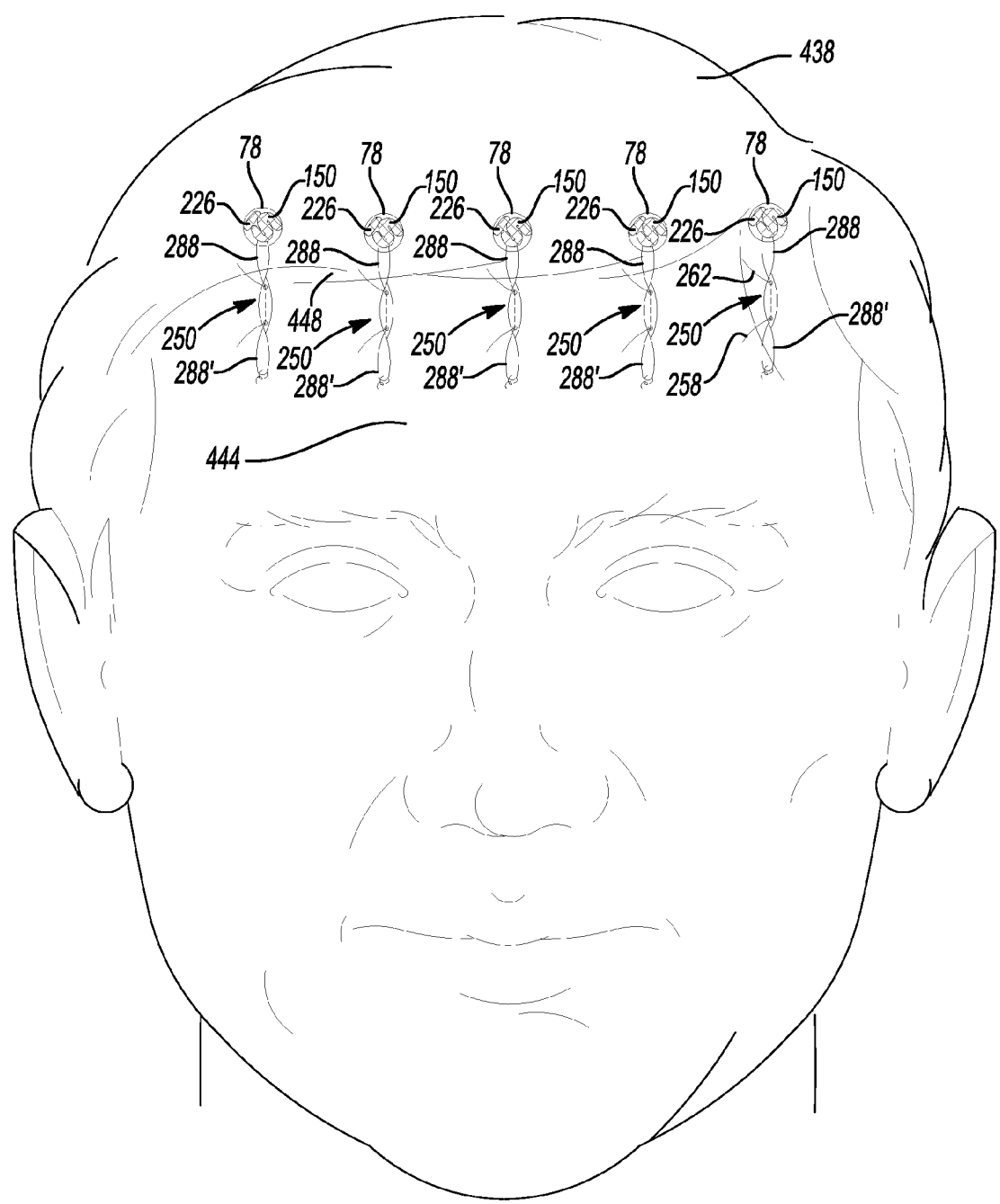
FIG. 23 is a view of an exemplary surgical technique for a facelift according to the present disclosure.

With additional reference to FIGS. 21-23, exemplary surgical techniques will now be discussed in greater detail in connection with inserter 86 and suture construct 300 coupled thereto. With particular reference to FIG. 22, an alternative technique for repairing the labral tear 22 can include coupling adjustable suture construct 300 to inserter 350 such that the flexible anchor 150 associated with the passage portion 268 is coupled to the distal tip 146 of elongate member 94 and the other flexible anchor extends freely therefrom, as shown in FIG. 21. The elongate member 94 can then be inserted into and through labrum 18 and into bore 78 prepared in the manner discussed above. It should be appreciated that guide 30 can be used with elongate member 94, if desired. Inserter 86 can then be axially moved relative to bore 78 and labrum 18 to deploy anchor 150 associated with passage portion 268 into bore 78. Inserter 86 can then be removed from bore 78 and labrum 18, and suture ends 258, 262 can be decoupled from protrusion 118. Suture construct 300 can now be positioned such that the flexible anchor 150 associated with the passage portion 268 is positioned in bore 78 and portions of loops 304, 304', as well as free ends 258, 262 extend from bore 78 and through labrum 18, as shown in FIG. 22.

The free ends 258, 262 extending from labrum 18 can be tensioned to reduce the size of loops 304, 304' and set the flexible anchor 150 in bore 78 in the manner discussed above. Further tensioning of suture construct 300 can continue to reduce the size of loops 304, 304' thereby compressing flexible anchor 150 associated with summit portions 308, 308' against the exterior surface of labrum 18 and tightly securing labrum 18 against glenoid 14 with using a knot. It should be appreciated that during tensioning of suture construct 300, passage portion 268 and summit portions 308, 308' slide relative to the respective flexible anchors 150. While the above surgical technique has been described in connection with implanting one suture construct 300, it should be appreciated that multiple suture constructs 300 and/or combinations of suture constructs 84, 250 and 300 can be used in the surgical technique.

Turing now to FIG. 23, an exemplary surgical technique for a facelift will now be described with reference to inserter 86 and suture constructs 250 and 300. In one exemplary configuration shown in FIG. 23, suture construct 250 can be modified so as to include only one flexible anchor 150 that is coupled to loop 288 while loop 288' does not include a flexible anchor. The modified suture construct 250 can be coupled to inserter 86 in a similar manner as discussed above in connection with FIG. 21 such that flexible anchor 150 associated with loop 288 can be coupled to elongate member 94 loop 288' can extend freely therefrom. At least one bore 78 can be prepared in a skull 438 of the patient similar to the preparation of bore 78 in glenoid 14. The elongate member 94 of inserter 86 can then be inserted into bore 78 to position flexible anchor 150 therein. It should be appreciated that elongate member 94 can be inserted into bore 78 with or without the use of guide 30 for this procedure.

Inserter 86 can then be translated relative to skull 438 to deploy flexible anchor 150 in a similar manner as discussed above. Once anchor 150 is deployed, inserter 86 can be removed from bore 78 and free ends 258, 262 can be decoupled from protrusion 118 and inserter 86. Loop 288' can then be temporarily coupled to an appropriate position of the skin of the forehead 444 proximate the patient's hairline 448 with suture or other appropriate methods, as shown in FIG. 23. Once loops 288, 288' are secured to the skull 438 and forehead skin 444, free ends can be tensioned to reduce the size of loops 288, 288' to set anchor 150 and stretch the forehead skin 444 towards the bore 78 by any appropriate amount. It should be appreciated that anchor 150 can be set as described immediately above or before loops 288, 288' ends 258, 262 are tensioned to reduce the size of loops 288, 288'. While the above surgical technique has been described in connection with implanting one suture construct 250, it should be appreciated that multiple suture constructs 250 and/or combinations of suture constructs 250 and 300 can be used in this surgical technique. While the above surgical technique has been described with reference to the forehead skin 444, it should be appreciated that other areas of facial skin can be coupled to loop 288' to stretch or reconfigure the facial skin as discussed above with reference to the forehead skin.

While one or more specific examples have been described and illustrated, it will be understood by those skilled in the art that various changes may be made and equivalence may be substituted for elements thereof without departing from the scope of the present disclosure as defined in the claims. Furthermore, the mixing and matching of features, elements and/or functions between various examples may be expressly contemplated herein so that one skilled in the art would appreciate from the present disclosure that features, elements and/or functions of one example may be incorporated into another example as appropriate, unless described otherwise above. Moreover, many modifications may be made to adapt a particular situation or material to the present disclosure without departing from the essential scope thereof.

What is claimed is:

1. A method for securing soft tissue to bone, comprising:
   forming a bore in the bone;
   carrying a flexible anchor into the bore, the flexible anchor including a passage and being coupled to a suture construct, the suture construct including a suture having first and second free ends, a body defining a passage portion and at least one self-locking adjustable loop, at least one of the first or second free ends passing through the passage portion of the body to form the self-locking adjustable loop, the flexible anchor coupled to the suture construct by the first or second free end of the suture construct extending through an intermediate portion of the passage spaced apart from respective ends of the flexible anchor such that the flexible anchor is coupled to the at least one self-locking adjustable loop and is slidable relative thereto, where portions of the flexible anchor between the intermediate portion and each end define anchoring leg portions free of the suture, the flexible anchor including a first profile while being carried into the bore;

changing a shape of the flexible anchor from the first profile to a second profile forming an anchoring mass to retain the flexible anchor in the bore; and applying tension to a portion of the suture construct to reduce a size of the self-locking adjustable loop and secure the soft tissue relative to the flexible anchor and the bone and maintain the reduced size of the self-locking adjustable loop in an absence of a knot.

2. The method of claim 1, wherein changing a shape of the flexible anchor includes collapsing the flexible anchor from the first profile to the anchoring mass of the second profile, wherein the anchoring mass includes a width in a direction perpendicular to a longitudinal axis of the bore greater than the first profile.

3. The method of claim 2, wherein forming a bore in bone includes forming a bore through a cortical layer of the bone and into a cancellous layer of the bone; and
wherein changing a shape of the flexible anchor includes seating the anchoring mass against the cortical layer of the bone.

4. The method of claim 3, wherein changing a shape of the flexible anchor includes forming the anchoring mass where the width is greater than a width of the bore through the cortical layer of the bone.

5. The method of claim 1, wherein carrying a flexible anchor into the bore includes carrying a tubular flexible anchor into the bore, wherein the flexible anchor is formed from a woven or braided suture material.

6. The method of claim 1, wherein applying tension to a portion of the suture construct to reduce a size of the self-locking adjustable loop and secure the soft tissue relative to the flexible anchor and the bone includes sliding the suture construct relative to the flexible anchor in the formed anchor mass of the second profile.

7. The method of claim 1, wherein carrying a flexible anchor into the bore includes coupling the flexible anchor to a distal tip of an inserter instrument.

8. The method of claim 7, further comprising:
positioning a cannulated guide member relative to the bore; and
inserting the inserter instrument having the flexible anchor coupled thereto into the guide member to guide the distal tip of the inserter instrument into the bore.

9. The method of claim 7, further comprising routing a portion of the suture construct through a recess in a handle of the inserter instrument and through a protrusion in the handle having a removable securing member configured to removable secure the suture construct to the protrusion and facilitate retaining the flexible anchor relative to the distal tip.

10. The method of claim 1, wherein forming a bore in the bone includes forming a bore in a portion of glenoid bone.

11. The method of claim 10, wherein applying tension to a portion of the suture construct to reduce a size of the self-locking adjustable loop and secure the soft tissue relative to the flexible anchor and the bone includes securing a portion of a labrum to the glenoid bone.

12. The method of claim 1,
wherein the suture construct includes the first free end passing into and through the passage portion to form a first self-locking adjustable loop and the second free end passing into and through the passage portion in an opposite direction as the first end to form a second self-locking adjustable loop.

13. The method of claim 12, wherein applying tension to a portion of the suture construct to reduce a size of the self-locking adjustable loop includes applying tension to the free ends to pull first and second portions of the suture construct passing through the passage portion in opposite directions relative to the passage portion to reduce a size of the first and second self-locking adjustable loops and secure the soft tissue to the bone.

14. The method of claim 12, wherein the flexible anchor includes first and second flexible anchors coupled to the respective first and second self-locking adjustable loops.

15. The method of claim 14, wherein forming a bore in the bone includes forming a first bore and a second bore in the bone;
wherein carrying a flexible anchor into the bore includes carrying the first flexible anchor into the first bore and carrying the second flexible anchor into the second bore to position the suture construct relative to the soft tissue; and
wherein applying tension to a portion of the suture construct includes applying tension to the first and second ends to reduce a size of the first and second self-locking adjustable loops thereby changing the shape of the first and second flexible anchors to the anchoring mass of the second profile and securing the soft tissue to the bone.

16. The method of claim 12, wherein the flexible anchor includes first and second flexible anchors, the first flexible anchor being coupled to a summit portion of the first and second self-locking adjustable loops and the second flexible anchor being coupled to the passage portion, the summit portion being positioned opposite of the passage portion.

17. The method of claim 16, wherein carrying a flexible anchor into the bore includes inserting the second flexible anchor through the soft tissue and into the bore such that the passage portion is in the bore while the second flexible anchor remains outside of the soft tissue; and
wherein applying tension to a portion of the suture construct includes applying tension to the first and second ends to reduce a size of the first and second self-locking adjustable loops to secure the first flexible anchor in the bone and engage the second flexible anchor with a surface of the soft tissue to tightly secure the soft tissue relative to the first flexible anchor and the bone.

18. A method for securing soft tissue to bone, comprising:
forming a bore in the bone;
providing a suture construct, including:
a suture having first and second free ends and a body defining a passage portion;
first and second flexible suture anchors each having a first end and a second end;
the first and second flexible anchors coupled to the suture by a portion of the suture extending through first and second openings in each flexible anchor, where the first and second openings are between and spaced apart from the first and second ends to form first and second flexible anchoring legs free of the suture for each flexible anchor;
the first and second free ends of the suture extending into and through the passage portion of the body in opposite directions to form first and second self-locking adjustable loops;
carrying the first flexible suture anchor into the bore, the first flexible anchor including a first profile while being carried into the bore;
changing a shape of the first flexible anchor from the first profile to a second profile forming an anchoring mass to retain the first flexible anchor in the bore; and applying tension to the first and second ends of the suture construct to reduce a size of the first and second self-locking adjustable loops and secure the soft tissue relative to the first flexible anchor and the bone and maintain the reduced size of the first and second self-locking adjustable loops in an absence of a knot.

19. The method of claim 18, wherein the first and second flexible anchors being coupled to the suture includes coupling the first flexible anchor to the passage portion of the suture construct and coupling the second flexible anchor to a summit portion of the first and second self-locking adjustable loops, the summit portion being positioned opposite of the passage portion.

20. The method of claim 18, wherein applying tension to the first and second ends of the suture construct to reduce a size of the first and second self-locking adjustable loops and secure the soft tissue relative to the first flexible anchor and the bone includes sliding the first loop relative to the first flexible anchor in the second profile and the second loop relative to the second flexible anchor.

21. The method of claim 18, wherein forming a bore in the bone includes forming first and second bores in the bone;
wherein carrying the first flexible suture anchor into the bore includes carrying the first flexible anchor into the first bore and carrying the second flexible anchor into the second bore to position the suture construct relative to the soft tissue; and
wherein applying tension to the first and second ends of the suture construct to reduce a size of the first and second self-locking adjustable loops includes applying tension to the first and second ends of the suture construct to reduce a size of the first and second self-locking adjustable loops and secure the soft tissue relative to the first and second flexible anchors secured in the respective first and second bores.

22. A method for securing a labrum to a glenoid bone, comprising:
positioning a cannulated guide instrument on the glenoid bone;
passing a drill bit through the cannulated guide instrument to drill a bore in the glenoid bone;
inserting an inserter instrument into the cannulated guide instrument, the inserter instrument carrying a flexible anchor having a first end and a second end with a suture passed through a first opening and a second opening in the flexible anchor, where the first and second openings are between and spaced apart from the first and second ends to form first and second flexible anchoring legs free of the suture;
inserting the flexible anchor having a first profile into the bore in the glenoid bone;
changing a shape of the flexible anchor from the first profile to a second profile to form an anchoring mass to retain the flexible anchor in the bore; and
attaching the suture to the labrum to secure the labrum to the glenoid bone.

23. The method of claim 22, further comprising viewing through a window in a distal end of the cannulated guide instrument when drilling the bore in the glenoid bone with the drill bit and when inserting the flexible anchor into the bore with the inserter instrument.

24. The method of claim 22, wherein attaching the suture to the labrum to secure the labrum to the glenoid bone, further includes positioning the suture on lateral sides of the labrum to secure the labrum separated from a surface of the glenoid bone to the glenoid bone.

25. The method of claim 22, further comprising maintaining a distal end of the cannulated guide instrument on the glenoid bone at the same location when both passing the drill bit through the cannulated guide instrument and when inserting the inserter instrument into the cannulated guide instrument.

26. The method of claim 22, wherein inserting the flexible anchor into the bore includes impacting the inserter instrument with a mallet to insert the flexible anchor that is folded about mid-length over a distal end of the inserter instrument into the bore in the glenoid bone.

27. The method of claim 22, wherein changing the shape of the flexible anchor from the first profile to the second profile includes expanding a width of the flexible anchor upon forming the anchoring mass, such that the width in the second profile is greater than the width in the first profile.

28. The method of claim 22, further comprising releasing the suture from a handle on the inserter instrument, where the suture is retained in a groove on the handle, to allow tensioning of the suture to change the shape of the flexible anchor from the first profile to the second profile.

29. The method of claim 22, wherein the suture is a suture construct that includes a first self-locking adjustable loop and a second self-locking adjustable loop and the flexible anchor is coupled to at least one of the first and second self-locking adjustable loops.

30. The method of claim 29, wherein the suture has first and second free ends and a body defining a passage portion where the first end is passed into and through the passage portion to form the first self-locking adjustable loop and the second end is passed into and through the passage portion in an opposite direction to form the second self-locking adjustable loop.

31. A method for securing soft tissue to bone, comprising:
forming a suture construct, including:
providing a suture having first and second free ends and a body extending therebetween and defining a passage portion;
providing first and second flexible suture anchors each having a passage;
coupling the first and second flexible anchors to the suture by inserting at least one free end of the suture through an intermediate portion of the passage of each flexible anchor spaced apart from respective ends of the flexible anchor such that portions of each flexible anchor between the intermediate portion and each end define anchoring leg portions free of the suture; and
passing the first and second free ends of the suture into and through the passage portion of the body in opposite directions to form first and second self-locking adjustable loops.

32. The method of claim 31, wherein coupling the first and second flexible anchors to the suture includes coupling the first flexible anchor to the passage portion of the suture construct and coupling the second flexible anchor to a summit portion of the first and second self-locking adjustable loops, the summit portion being positioned opposite of the passage portion.

33. The method of claim 32, further comprising:
forming a bore in the bone;
carrying the first flexible suture anchor into the bore, the first flexible anchor including a first profile while being carried into the bore;
changing a shape of the first flexible anchor from the first profile to a second profile forming an anchoring mass to retain the first flexible anchor in the bore; and
applying tension to the first and second ends of the suture construct to reduce a size of the first and second self-locking adjustable loops and secure the soft tissue relative to the first flexible anchor and the bone.

34. The method of claim 33, wherein forming a bore in the bone includes forming first and second bores in the bone;
wherein carrying the first flexible suture anchor into the bore includes carrying the first flexible anchor into the first bore and carrying the second flexible anchor into the second bore to position the suture construct relative to the soft tissue; and
wherein applying tension to the first and second ends of the suture construct to reduce a size of the first and second self-locking adjustable loops includes applying tension to the first and second ends of the suture construct to reduce a size of the first and second self-locking adjustable loops and secure the soft tissue relative to the first and second flexible anchors secured in the respective first and second bores.

35. The method of claim 33, wherein forming a bore in the bone includes forming a bore in a portion of glenoid bone.

\* \* \* \* \*